US009441253B2

(12) United States Patent
San et al.

(10) Patent No.: US 9,441,253 B2
(45) Date of Patent: Sep. 13, 2016

(54) METABOLIC TRANSISTOR IN BACTERIA

(71) Applicant: William Marsh Rice University, Houston, TX (US)

(72) Inventors: Ka-Yiu San, Houston, TX (US); George N. Bennett, Houston, TX (US); Hui Wu, Houston, TX (US)

(73) Assignee: William Marsh Rice University, Houston, TX (US)

( * ) Notice: Subject to any disclaimer, the term of this patent is extended or adjusted under 35 U.S.C. 154(b) by 130 days.

(21) Appl. No.: 14/176,008

(22) Filed: Feb. 7, 2014

(65) Prior Publication Data
US 2014/0227745 A1 Aug. 14, 2014

Related U.S. Application Data

(60) Provisional application No. 61/763,019, filed on Feb. 11, 2013.

(51) Int. Cl.
| | |
|---|---|
| *C12P 13/22* | (2006.01) |
| *C12P 7/56* | (2006.01) |
| *C12P 7/54* | (2006.01) |
| *C12P 13/18* | (2006.01) |
| *C12P 13/08* | (2006.01) |
| *C12P 13/06* | (2006.01) |
| *C12N 15/52* | (2006.01) |
| *C12N 9/02* | (2006.01) |
| *C12N 9/10* | (2006.01) |
| *C12N 9/80* | (2006.01) |
| *C12N 9/88* | (2006.01) |
| *C12N 9/00* | (2006.01) |
| *C12P 1/04* | (2006.01) |
| *C12P 7/06* | (2006.01) |
| *C12P 7/18* | (2006.01) |
| *C12P 7/40* | (2006.01) |
| *C12P 7/46* | (2006.01) |
| *C12P 13/04* | (2006.01) |
| *C12P 13/14* | (2006.01) |

(52) U.S. Cl.
CPC ............. *C12P 13/225* (2013.01); *C12N 9/001* (2013.01); *C12N 9/0008* (2013.01); *C12N 9/0073* (2013.01); *C12N 9/1085* (2013.01); *C12N 9/80* (2013.01); *C12N 9/88* (2013.01); *C12N 9/93* (2013.01); *C12N 15/52* (2013.01); *C12P 1/04* (2013.01); *C12P 7/065* (2013.01); *C12P 7/18* (2013.01); *C12P 7/40* (2013.01); *C12P 7/46* (2013.01); *C12P 7/54* (2013.01); *C12P 7/56* (2013.01); *C12P 13/04* (2013.01); *C12P 13/06* (2013.01); *C12P 13/08* (2013.01); *C12P 13/14* (2013.01); *C12P 13/18* (2013.01); *C12P 13/222* (2013.01); *C12Y 102/01025* (2013.01); *C12Y 102/04004* (2013.01); *C12Y 102/07007* (2013.01); *C12Y 103/01076* (2013.01); *C12Y 103/05005* (2013.01); *C12Y 114/13027* (2013.01); *C12Y 205/01001* (2013.01); *C12Y 205/01032* (2013.01); *C12Y 205/01093* (2013.01); *C12Y 305/01022* (2013.01); *C12Y 305/99002* (2013.01); *C12Y 401/01024* (2013.01); *C12Y 602/01011* (2013.01); *Y02E 50/17* (2013.01); *Y02P 20/52* (2015.11)

(58) Field of Classification Search
CPC .................................. C12P 7/56; C12N 15/70
USPC .................... 435/108, 111, 115, 116, 252.33
See application file for complete search history.

(56) References Cited

U.S. PATENT DOCUMENTS

2004/0152159 A1    8/2004    Causey

OTHER PUBLICATIONS

Wu et al. Biotechnology and bioengineering, (Aug. 2015) vol. 112, No. 8, pp. 1720-1726.*
Alper H., Miyaoku K., Stephanopoulos G., (2005) Construction of lycopene overproducing E. coli strains by combining systematic and combinatorial gene knockout targets. Nat. Biotechnol. 23,612-616.
Blombach B. et al., (2007) I-Valine Production with Pyruvate Dehydrogenase Complex-Deficient Corynebacterium glutamicum, Appl. Environ. Microbiol. 73(7): 2079-2084.
Borisov VB, Gennis RB, Hemp J, Verkhovsky MI (2011) The cytochrome bd respiratory oxygen reductases. Biochim Biophys Acta 1807: 1398-1413.
Cunningham F.X. Jr., et al., (1994) Molecular structure and enzymatic function of lycopene cyclase from the cyanobacterium Synechococcus sp strain PCC7942. Plant Cell 6:1107-1121.
Farmer W.R., Liao J.C., (2000) Improving lycopene production in Escherichia coli by engineering metabolic control. Nat. Biotechnol. 18, 533-537.
Hassan BH, Cronan JE (2011) Protein-protein interactions in assembly of lipoic acid on the 2-oxoacid dehydrogenases of aerobic metabolism. J. of Biol. Chem. 286: 8263-8276.
Hermes FA, Cronan JE (2009) Scavenging of cytosolic octanoic acid by mutant LpIA lipoate ligases allows growth of Escherichia coli strains lacking the LipB octanoyltransferase of lipoic acid synthesis. Journal of bacteriology 191: 6796-6803.
Iram SH, Cronan JE (2006) The beta-oxidation systems of Escherichia coliand Salmonella enterica are not functionally equivalent. Journal of bacteriology 188: 599-608.
Kameda K, Imai Y (1985) Isolation and characterization of the multiple charge isoforms of acyl-CoA synthetase from Escherichia coli. Biochim Biophys Acta 832: 343-350.

(Continued)

Primary Examiner — Tekchand Saidha
(74) Attorney, Agent, or Firm — Boulware & Valoir

(57) ABSTRACT

The disclosure relates to a metabolic transistor in bacteria where a competitive pathway is introduced to compete with a product pathway for available carbon so as to control the carbon flux in the bacteria.

7 Claims, 7 Drawing Sheets

(56) References Cited

OTHER PUBLICATIONS

Londer YY (2011) Expression of recombinant cytochromes c in *E. coli*. Methods Mol Biol 705: 123-150.

Lu P., (2007) Absolute protein expression profiling estimates the relative contributions of transcriptional and translational regulation. Nature Biotechnol. 25: 117-124.

Morris T.W., (1995) Lipoic acid metabolism in *Escherichia coli*: the IpIA and lipB genes define redundant pathways for ligation of lipoyl groups to apoprotein. Journal of bacteriology 177: 1-10.

Perham RN (1991) Domains, motifs, and linkers in 2-oxo acid dehydrogenase multienzyme complexes: a paradigm in the design of a multifunctional protein. Biochem. 30:8501-8512.

Peters-Wendisch P., (2012) Biotin protein ligase from Corynebacterium glutamicum: role for growth and L:-lysine production, Appl, Microbiol, Biotechnol. 93(6):2493-502.

Reed K.E., Cronan J.E., Jr. (1993) Lipoic acid metabolism in *Escherichia coli*: sequencing and functional characterization of the lipA and lipB genes. J. Bacteriol. 175:1325-1336.

Schellhorn H.E, Hassan H.M. (1988) Isolation and characterization of respiratorydeficient mutants of *Escherichia coli* K-12. J. Bacteriol. 170: 78-83.

Spencer JB, Stolowich NJ, Roessner CA, Scott AL (1993) The *Escherichia coli* cysG gene encodes the multifunctional protein, siroheme synthase. FEBS Lett. 335: 57-60.

Stolz M, et al., (2007) Reduced folate supply as a key to enhanced L-serine production by Corynebacterium glutamicum, Appl. Environ. Microbiol. 73(3):750-5.

Taboada, H., et al. (2008) Thiamine limitation determines the transition from aerobic to fermentative-like metabolism in Rhizobium etli CE3, FEMS Microbiology Letters 279(1): 48-55.

Thony-Meyer L (1997) Biogenesis of respiratory cytochromes in bacteria. Microbiol. Mol. Biol. Rev. 61: 337-376.

Tsai C.H., et al., (2000) Novel recombinant hemoglobin, rHb (beta N108Q), with low oxygen affinity, high cooperativity, and stability against autoxidation. Biochem. 39: 13719-13729.

Vadali R.V., et al., (2005) Enhanced lycopene productivity by manipulation of carbon flow to isopentenyl diphosphate in *Escherichia coli*, Biotechnol. Prog. 21, 1558-1561.

Varnado C.L., et al., (2013) Development of recombinant hemoglobin-based oxygen carriers, Antioxid. Redox Signal 18:2314-2328.

Warren M.J., et al., (1994) Gene dissection demonstrates that the *Escherichia coli* cysG gene encodes a multifunctional protein, Biochem J 302(Pt 3): 837-844.

Warren M.J., et al., (1990) The *Escherichia coli* cysG gene encodes Sadenosylmethionine-dependent uroporphyrinogen III methylase, Biochem J. 265: 725-729.

Yazaki K., et al., (2002) Geranyl diphosphate:4-hydroxybenzoate geranyltransferase from Lithospermum erythrorhizon. Cloning and characterization of a key enzyme in shikonin biosynthesis, J. Biol. Chem. 277, 6240-6246.

\* cited by examiner

ETC = electron transfer chain.

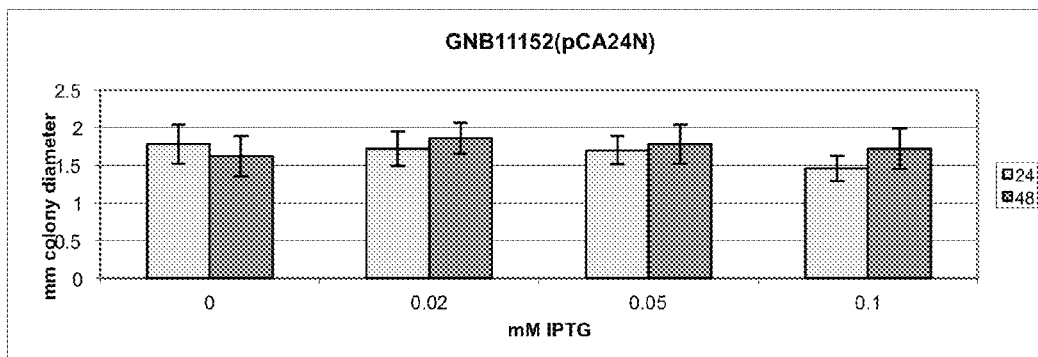

FIG. 7A

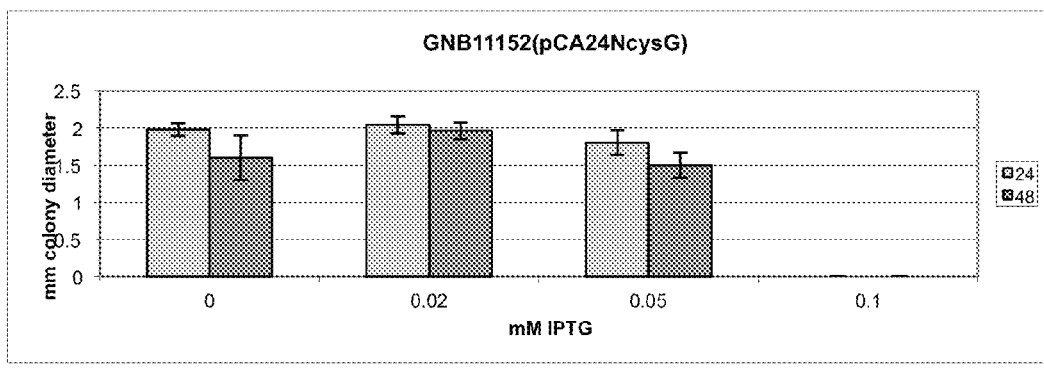

FIG. 7B

| | GNB11152 | GNB11152 (pCA24N-cysG) |
|---|---|---|
| Lactate level after 6 hours | 0.27 mM | 0.77mM |
| Concentration of inducer IPTG | 0.07 mM | 0.09 mM |
| Cell density Abs 600nm | 0.76 | 0.72 |
| Cells of GNB11152 containing the cysG plasmid pCA24N-cysG were grown using a 1% inoculum into LB with 0.2% glucose. In cultures where no inducer was added no lactate was observed in the 6 hr samples. Increased lactate compared to control cells is observed when heme is limited by this diverting gene. | | |

FIG. 8

METABOLIC TRANSISTOR IN BACTERIA

PRIOR RELATED APPLICATIONS

This application claims priority to U.S. Provisional Appln. No. 61/763,019, filed Feb. 11, 2013, and expressly incorporated by reference in its entirety herein for all purposes.

FEDERALLY SPONSORED RESEARCH STATEMENT

This invention was made with government support under Grant No: R01 GM090152 awarded by the NIH. The government has certain rights in the invention.

FIELD OF THE DISCLOSURE

The disclosure generally relates to methods of finely controlling the metabolism of a cell by introducing a diverting pathway for a key molecule in a competitive pathway that otherwise competes with and reduces the level of a desired product. The diverting pathway is under the control of a controllable promoter, such that expression of the diverting pathway can be finely tuned, thus controlling the diversion of the key molecule and hence the related competitive pathway. Slowing down the competitive pathway allows increased production of product.

BACKGROUND OF THE DISCLOSURE

All living creatures, be it man or the smallest bacteria have one function in common known as respiration. During respiration, two important functions are performed in living things. In the first, electrons that were generated during catabolism are disposed of and in the second, ATP (also known as adenosine tri-phosphate) is produced to provide energy for the cell.

There are two types of respiration: (i) aerobic respiration and (ii) anaerobic respiration. Aerobic respiration requires oxygen, but oxygen is not required for anaerobic respiration, often called "fermentation" in bacteria. Instead, other less-oxidizing substances such as sulfate ($SO_4^{2-}$), nitrate ($NO_3^-$), sulfur (S), or fumarate are used. These terminal electron acceptors have smaller reduction potentials than $O_2$, meaning that less energy is released per oxidized molecule. Anaerobic fermentation is, therefore, energetically less efficient than aerobic respiration. Nonetheless, it has value and allows the cells to continue living even with no or reduced $O_2$.

Anaerobic fermentation and aerobic respiration have been the two metabolic modes of interest for the industrial production of chemicals from microbes such as E. coli, Lactobacillus and yeast. Oxygen rich respiration offers very efficient cell growth (growth rate and yield) and converts a high percentage of the carbon source into carbon dioxide and cell mass (see Table 1). Anaerobic fermentation, on the other hand, results in poor cell growth and the synthesis of several fermentation products at high yields (e.g. lactate, formate, ethanol, acetate, succinate, etc.).

However, producing chemicals via oxygen rich processes costs much more than using anaerobic methods for two reasons. First, aerobic fermenters are more expensive to build, due to both the higher cost per unit and the need for smaller fermenters with reduced economy of scale. Secondly, the aerobic fermenters are more costly to operate than their anaerobic counterparts due to low solubility of oxygen, which in turn requires high energy input to ensure appropriate supply of oxygen to the cells. This is especially relevant for the production of commodity chemicals, where fermentation costs can represent 50-90% of the total production cost.

TABLE 1

RESPIRATORY VS FERMENTATIVE METABOLISM

| Variable | Anaerobic Fermentation | Anaerobic Respiration | Aerobic Respiration |
|---|---|---|---|
| Growth Rate | LOW | Intermediate | HIGH |
| Cell Mass | LOW | Intermediate | HIGH |
| Product Yields | HIGH | High/Intermediate | LOW |
| Capital Cost | LOW | LOW | HIGH |
| Energy Input | LOW | LOW | HIGH |

Therefore, anaerobic methods are usually preferred where possible, and it is typical to grow cells to a large number aerobically, and then switch the cells to anaerobic culture for the production of desired chemicals. Often, however, the method is less than completely successful, resulting in poor yields and rates.

US20100317086 describes a three-stage process, where the bacteria are first acclimated to low $O_2$ conditions before switching to anaerobic conditions, and this helps to improve yields of various biological chemicals.

However, there is still a need to maximize chemical production, while maintaining robust cell growth, and optimizing production yields. One way of optimizing yield is to directly attempt to increase the genes resulting in the desired product. Another method, would be to directly downregulate a competitive pathway. However, direct methods have limitations, can be difficult to fine tune, and are often not satisfactory. We introduce herein indirect methods of influencing flux, which are amenable to fine tuning

SUMMARY OF THE DISCLOSURE

We provide herein a completely novel strategy to finely control a metabolic flux by using a "metabolic transistor" approach. In this new approach, the pathway of interest converts glucose or other carbon source into a desired product P. However, a competitive pathway C, that uses cofactor F, competes for the same carbon sources, thus reducing the level of P that can be produced when C is active. If we add in certain diverting genes to compete with the competitive pathway C, it will allow increased P to be formed. Generally speaking, the diverting gene(s) will either directly compete for F (degrading it or using it for its own reactions) or will utilize a precursor of F. Cofactor F thus becomes rate limiting, slowing the competitive pathway C, and allowing more carbon to flow to P, and resulting in increasing levels of P.

The competitor flux is dependent on the presence of a cofactor or other key intermediate that is required for the competitive pathway, but not for P. Since the key intermediate is normally present in large enough amounts and may even have redundant means for its biosynthesis or uptake, it is not generally considered a key control point. However, if controlled in a fine-tuned amount around a threshold level, dramatic effects may be seen with a very small perturbation of the available level of the key intermediate. Thus, the addition of diverting pathways for the cofactor can allow fine control over the product pathways.

The principles of the current invention are:

1) The metabolic transistor concept that a competitive metabolic flux can be controlled by small changes in the level or availability of a cofactor require for the competitive flux (but not for P);

2) Cofactor levels in the competitive flux can be modulated by adding an exogenous diverting reaction that either directly reduces available cofactor or indirectly reduces a needed precursor for the cofactor;

3) Controlling the level of a competitive pathway (by controlling cofactor levels) with the added diverting gene(s) allows increased carbon flow though the desired pathway to P.

We exemplified the concept herein using ubiquinone as an example of a cofactor, where the competitive pathway is the electron transfer chain (ETC). In this case, the flow through the electron transfer chain can be controlled by controlling the size of the ubiquinone pool. Thus, we add diverting genes that siphon off precursors for ubiquinone, reducing the available ubiquinone, and thus reducing the activity of the ETC and thereby funneling carbons to the fermentative pathways, exemplified in this case by increased lactate formation. Of course, the addition of other mutants can shift the levels of the various fermentation products in desired directions, as is known in the art. See e.g., US20130203137, U.S. Pat. No. 7,790,416, US20130084600, US20130052705, U.S. Pat. No. 7,244,610, U.S. Pat. No. 7,927,859, U.S. Pat. No. 7,901,924, U.S. Pat. No. 8,236,525, US20100184195 (each incorporated by reference in its entirety).

Although we have exemplified this idea herein with the key intermediate ubiquinone and the diverting genes for lycopene synthesis, the invention can be more broadly applied wherever fine control over a pathway is desired. Several examples are provided herein.

The term "product" as used herein refers to a desired product that is made by a bacteria or yeast. "Product" or "P" is produced by a "product pathway" which can be a natural pathway, or a pathway that has been added to the cell by recombinant techniques.

The term "competitive pathway" refers to a pathway that makes "competitor" or "C" that competes with the product pathway for carbon resources, thus reducing the overall level and/or rate of desired product P produced. Thus, the substrate for pathway C ($S_c$) is converted to Competitor C. Of course, there can be one or more of such reactions, such that there are one or more intermediates in the pathway $I_c$, wherein c is an integer from 1 to n in the direct pathway to C. Thus, C Pathway=$S_c$>$I_{c=0-n}$>C Of course, to some extent every pathway in the cell is interconnected, but by competitor pathway, we mean a direct pathway from substrate to competitor product via one or more intermediates.

The competitive pathway has a "cofactor" or other "key intermediate" that is not normally rate limiting, but which could become rate limiting if a diverting pathway was added to directly or indirectly compete for same.

The term "diverting gene(s)" means one or more genes that expresses a protein that competes directly or indirectly for a cofactor or other key intermediate needed to operate a competitive pathway. Thus, the diverting gene(s) results in a lower concentration of cofactor or key intermediate when such gene(s) are expressed. This results in increased levels of the desired Product, which does not use the same cofactor or key intermediate in its pathway.

The term "cofactor" means a small molecule needed for one or more reactions in a pathway. The cofactor could control the overall level of the competitive pathway if its levels could be sufficiently controlled, although the cofactor itself is not normally rate limiting. The diverting genes can directly siphon off cofactor, or can indirectly siphon off a precursor in the biosynthesis of the cofactor.

The term "promoter" means a regulatory sequence allowing expression of the gene under the control, thereof. Tunable or "inducible promoters" are preferred for controlling the diverting gene(s). Inducible promoters are well known, and new ones are always being developed and can be selected as best suited to the bacteria of interest. For *E. coli*, one such promoter such as the lac promoter that responds to IPTG levels. Other suitable promoter systems could include the arabinose promoter (ara), which responds to arabinose levels; the tetracycline promoter (Tet), which responds to tetracycline levels; the luxI promoter, activated by N-3-oxohexanoyl-L-homoserine lactone (HSL); pL and/or pR phage lambda promoters, promoters induced by anaerobic conditions or stationary phase, acetate, phosphate levels, or other sugars like arabinose, rhamnose, or xylose. There are even light responsive promoters available in the art. A great number of promoters are listed at partsregistry.org/Cell-cell_signalling, and many more are available in various catalogs.

*E. coli* gene and protein names (where they have been assigned) can be ascertained through ecoliwiki.net/ and enzymes can be searched through brenda-enzymes.info/. ecoliwiki.net/ in particular provides a list of alternate nomenclature for each enzyme/gene. Many similar databases are available including UNIPROTKB, PROSITE; 5 EC2PDB; ExplorEnz; PRIAM; KEGG Ligand; IUBMB Enzyme Nomenclature; IntEnz; MEDLINE; and MetaCyc, to name a few.

We have typically used the gene and protein names from BRENDA herein, but not always. By convention, genes are written in italic, and corresponding proteins in regular font. E.g., fadD is the gene encoding FadD or acyl-CoA synthetase.

Generally speaking, we use the gene name and protein names interchangeably herein, based on the protein name as provided in BRENDA. The use of a protein name as an overexpressed protein (e.g., FabH+) signifies that protein expression can occur in ways other than by adding a vector encoding same, since the protein can be upregulated in other ways. The use of FadD⁻ signifies that the protein can be downregulated in similar way, whereas the use of ΔfadD means that the gene has been directly downregulated, e.g., by knockout or null mutation.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
|---|---|
| 3OC12-HSL | N-3-oxododecanoyl-HSL |
| 4-HB | 4-hydroxybenzoic acid, used interchangeably with 4-hydroxy benzoate |
| ara | Arabinose inducible promoter |
| CrtB | phytoene synthase, encoded by crtB |
| CrtE | geranylgeranyl diphosphate synthase, encoded by crtE |
| CrtI | phytoene desaturase, encoded by crtI |
| CysG | Siroheme synthase, multifunctional enzyme; has three activities: uroporphyrinogen III methyltransferase, SAM-dependent; precorrin-2 dehydrogenase; sirohydrochlorin ferrochelatase, encoded by cysG |
| DCW | Dry cell weight |
| ETC | Electron transport chain |
| FadD | acyl-CoA synthetase (long-chain-fatty-acid--CoA ligase), encoded by fadD aka ECK1803, b1805, JW1794, oldD |
| FadR | Represser/activator for fatty acid metabolism regulon, encoded by fadR aka ECK1175, b1187, JW1176, dec, ole, thdB, oleR |
| G-4HB | geranyl-4-hydrozybenzoate |
| HSL | fatty acyl-homoserine lactones |
| IPP | isopentenyl diphosphate |
| IPTG | Isopropyl-beta-D-thiogalactoside |
| Lac | IPTG inducible promoter |
| lePGT-1 | PGT gene from Lithospermum erythrorhizon |
| lyco+ | overexpression of CrtIBE from Erwinia herbicola in pACYC184 |
| pAC-LYC | Plasmid including crtI, crtE, and crtB, together CrtIBE (Based on pACYC184) |
| pACYC184 | Plasmid (not inducible) |
| pBAD33 | Plasmid under arabinose control |
| pBlePGT | Plasmid including PGT under control of arabinose inducible promoter |
| Pcad | pH inducible promoter |
| PGT | geranyl diphosphate: 4-hydroxybenzoate 3-geranyltransferase |
| PGT+ | Overexpression of PGT |
| pL | Temperature inducible promoter |
| Plas | Cell density, 3OC12-HSL responsive promoter |
| pR | Temperature inducible promoter |
| pTrc-lePGT | Plasmid including PGT under control of IPTG inducible promoter |
| Tac | IPTG inducible promoter |
| TET | Tetracycline inducible promoter |
| Trc | IPTG inducible promoter |
| ubiE | bifunctional 2-octaprenyl-6-methoxy-1,4-benzoquinone methylase and S-adenosylmethionine: 2-DMK methyltransferase, encoded by ubiE aka ECK3827, b3833, JW5581, yigO, menG, menH |
| ubiG | Component of 3-demethylubiquinone 3-methyltransferase, encoded by ubiG aka ECK2224, b2232, JW2226, yfaB, pufX |
| ubiX | 3-octaprenyl-4-hydroxybenzoate carboxy-lyase, encoded by ubiX, aka ECK2305, b2311, JW2308, dedF |

DESCRIPTION OF THE DRAWINGS

FIG. 2. Schematic diagrams of an introduced Diverting Gene(s) which reduces Cofactor, thus decreasing Competitor and thereby increasing Product.

FIG. 5. Schematic diagram of the plasmids employed in this disclosure.

FIG. 7 Heme diversion experiment, showing colony size on plates with different levels of inducer are shown after 24 or 48 hours. FIG. 7A: Heme diversion experiment results for GNB11152 (pCA24N); FIG. 7B: Heme diversion experiment results for GNB11152 (pCA24NcysG). Abbreviation: GNB11152 is BW25113, the Keio background host strain; pCAN24N is the vector; pCAN24NcysG contains the cysG gene under control of a lac regulated promoter. Cell growth is limited when heme is limited by this diverting gene.

FIG. 8. Heme diversion experiment, showing increase lactate production when heme is diverted.

DETAILED DESCRIPTION

We propose a new strategy based on network topology and indirect control of competitive pathways by introducing additional nodes where flow through the biosynthetic pathway of interest can be controlled by partitioning at these newly introduced nodes. In other words, we introduce a diverting pathway and use this diversion to negatively control the level of a key participant of a competitive pathway, and thus to slow the flux through a competitive pathway and thereby increasing the flux through the pathway of interest.

Figure 1:
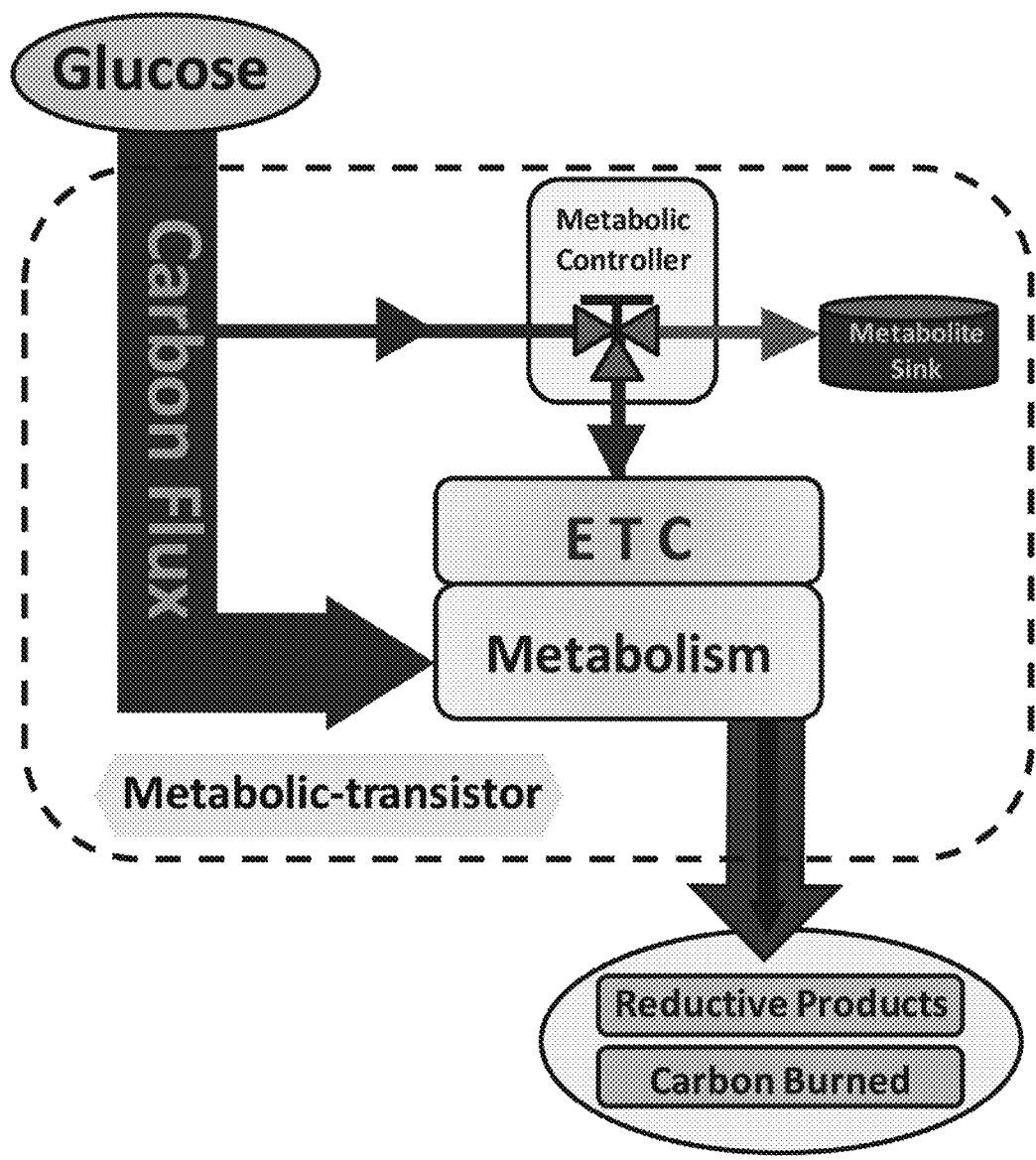
FIG. 1 Schematic diagram of a metabolic-transistor in bacteria. ETC=electron transfer chain.
Figure 2A:
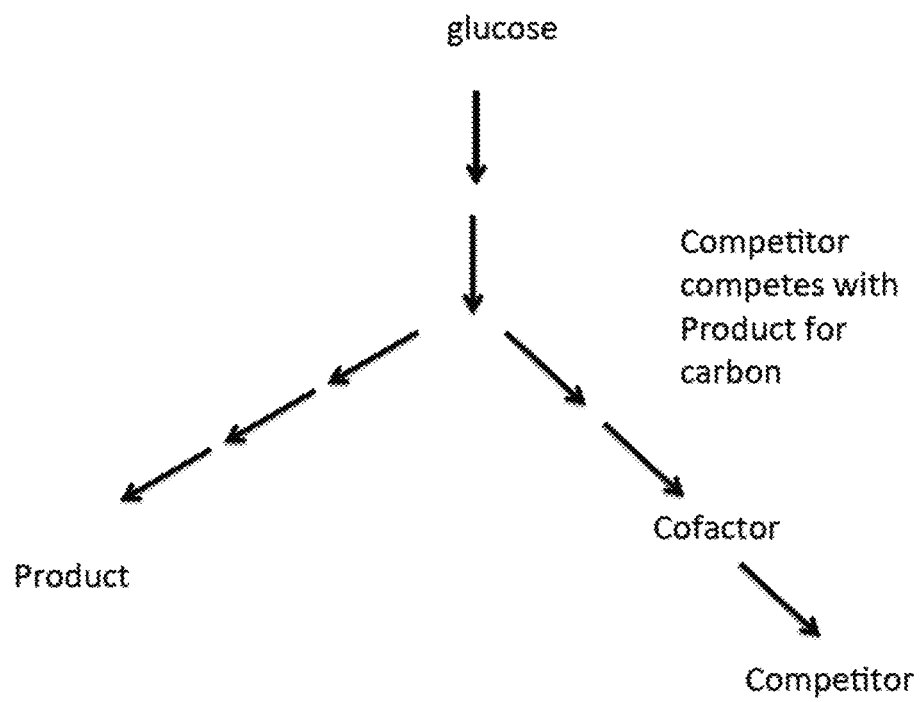
FIG. 2A is a schematic diagram of competitive pathway C which competes with product pathway P for carbon resources.
Figure 2B:
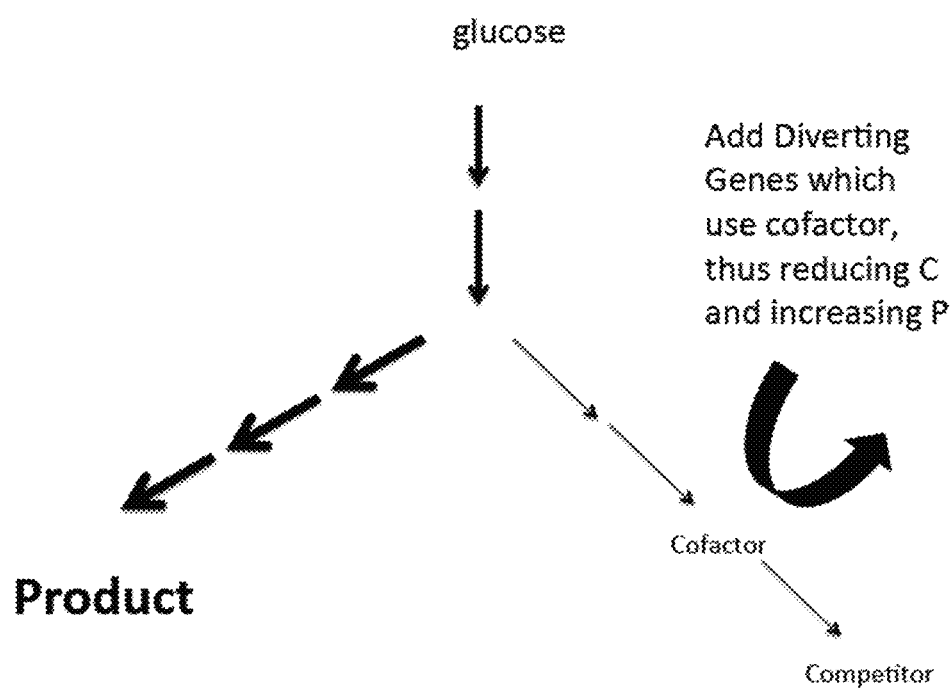
FIG. 2B shows the introduction of Diverting Gene(s), which divert cofactor away from C, thereby reducing flux to C and increasing flux to P.

FIG. 2A shows the desired pathway to product P that competes for carbon flow with the competitive pathway C. Adding diverting genes in FIG. 2B will divert cofactor or key intermediate in pathway C, thus slowing it and instead allowing the carbon flux to flow to P. Ideally, the relative amounts of the enzymes and their Km values need to be within an appropriate range relative to the cofactor or key intermediate. If these factors are within the appropriate range, the level of key intermediate can be reduced substantially by the presence of the new diverting reaction(s) and control of the level of key product P can be controlled over a small range.

In the case of the ETC, slowing the ETC pathway by adding diverting gene(s) to reduce ubiquinone levels allows the carbons to be channeled into fermentative pathways, even though $O_2$ is present. Thus, we can now take advantage of the high product yields that are available under fermentative conditions, even though $O_2$ is present.

There are many circumstances where it would be desired to control the amount of respiration, as shown herein. Too much respiration and oxidation of carbon substrates, while being beneficial for cell energetics and usually for growth rate, lead to loss of carbon that does not go into product (but into $CO_2$), especially if a reduced product is desired. Many reduced products of commercial interest, such as fuel molecules, are compounds more reduced than glucose, and many chemical intermediates for pharmaceuticals, lactate or monomers for making polymers, fatty acids, etc. also require reduction reactions and similarly need to limit oxidation of the feedstock for a high yield process.

It is difficult, however, to limit oxygen utilization in large reactors—that is to try to control the level of oxygen by feeding in say 1% oxygen and having this be constant and well distributed in the tank. A means of limiting the use of oxygen by the cell even when there is excess air or oxygen would thus be very useful.

We can control the level of expression of the diverting gene(s) by placing it under control of an inducible promoter that we can control by an added inducer compound. We could also use a static or constitutive promoter of the appropriate strength to keep the proportion at a desired level, however, fine tunable promoters are preferred, especially where external control via culture and media conditions is desired.

Other variations of this general concept could employ (1) adding enzymes that degrade or use up the key intermediate; (2) adding a protein that binds the key intermediate and sequesters it from entering into its normal function; (3) making or enhancing a pathway that consumes an intermediate of the key intermediate, thus competing it away by altering partitioning through the associated network connected to the biosynthetic pathway.

The advantage of this kind of indirect diversion approach is that it uses very little cell energy and protein quantity to control an important flux in the cell. This is akin to the way a transistor works, where a small current change is used to control a big current flow. The other advantage is that it can be very finely tuned for optimal or desired level performance. Thus, by making small changes in the availability of essential small cofactor or key component for the activity of the enzyme process, a big flow can be affected by subtle changes in the availability of the key intermediate or cofactor.

Ubiquinone Diversion

To exemplify the inventive concept, we have established a metabolic transistor control strategy on respiratory chain and internal redox levels based on manipulation of the quinone synthesis pathway in *E. coli*.

*E. coli* cells regenerate $NAD^+$ and generate proton motive force for ATP production through the respiratory chain. Quinones are lipid-soluble molecules that mediate electron transfer between NADH or FADH dehydrogenases and cytochrome oxidases. The major substrate precursor compounds of ubiquinone synthesis are polyprenyl diphosphate and 4-hydroxybenzoic acid (4-HB). The polyprenyl diphosphate is formed by a combination of multiple units of isopentenyl diphosphate (IPP) by polyprenyl diphosphate synthase.

Based on the quinone synthesis pathway, two strategies of controlling quinone synthesis can be applied in this invention (FIG. 3), where the thick arrow represents the strategy of using lycopene synthesis pathway as the diverting genes, and the dashed arrow represents the strategy of using the 4-hydroxybenzoate geranyltransferase gene (PGT) as a diverting gene. Either added pathway competes away precursors needed for synthesis of ubiquinone, thus reducing ETC by limiting available ubiquinone, which is not normally rate limiting.

The accession numbers for the various sequences discussed herein are as follows:

| Strain | Gene | GenBank Accession or Gene ID | Protein_ID |
| --- | --- | --- | --- |
| *Erwinia herbicola* | crtB | JX871356 | AFX61742.1 |
| *Erwinia herbicola* | crtE | JX871355 | AFX61741.1 |
| *Erwinia herbicola* | crtI | JX871357 | AFX61743.1 |
| *Lithospermum erythrorhizon* | lepgt-1 | AB055078 | BAB84122.1 |
| *Eschehchia coli* | ubiX | 948926 | AAC75371.1 |
| *Eschehchia coli* | ubiE | 949033 | AAT48227.1 |
| *Eschehchia coli* | ubiG | 946607 | AAC75292.1 |

Figure 3:
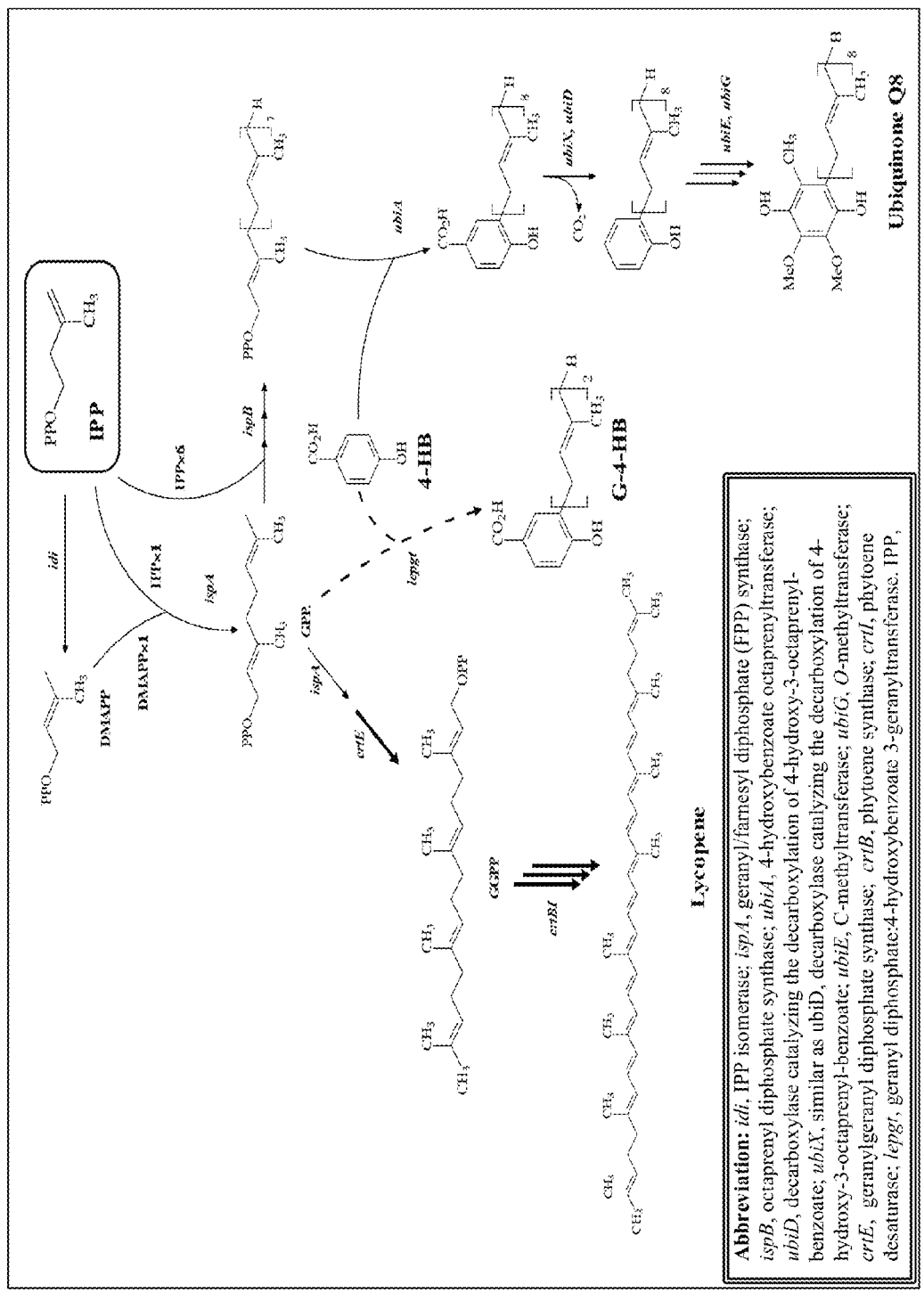
FIG. 3. Manipulation of ubiquinone synthesis pathway as a controller of the respiratory chain in bacteria. Strategy one: thick arrow pathway introduced into E. coli cell; strategy two: dash arrow pathway introduced into E. coli cell.

One demonstrated example of the inventive technique is using the lycopene synthesis pathway to drain a common substrate—isopentenyl diphosphate (IPP) (FIG. 3).

Figure 4:
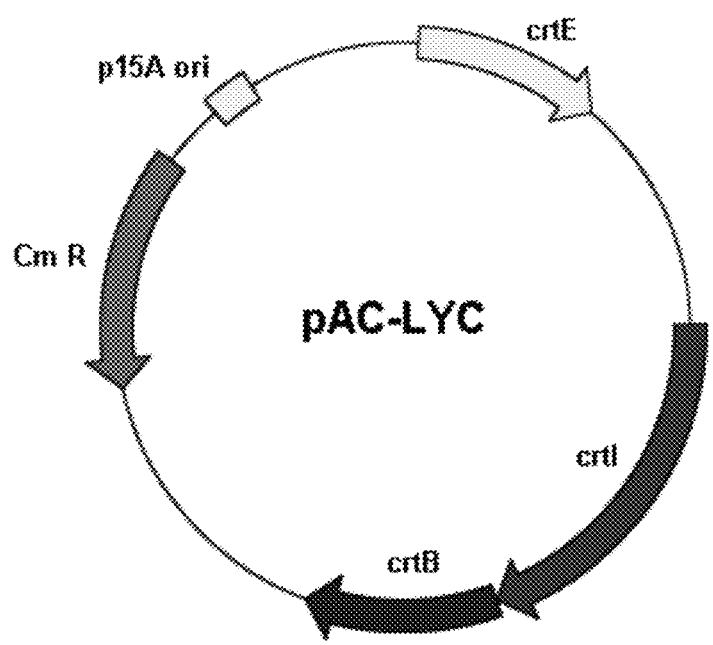
FIG. 4. Schematic diagram of the plasmid pAC-LYC. lycopene pathway genes including crtE=gene for geranylgeranyl diphosphate synthase; crtB=gene for phytoene synthase; crtI=gene for phytoene desaturase.

In previous studies, it was demonstrated that 1 mol of lycopene (C40) needed 8 mol of IPP (C5). The lycopene synthesis pathway thus can be a competing pathway on the common substrate, IPP, of the quinone synthesis pathway. Therefore we transformed the plasmid, which contained the lycopene production operon (crtB, crtE, crtI), into different genetic type *E. coli* strains to enhance the lycopene production pathway (FIG. 4), thus effectively competing away IPP, as desired based on the amount of promoter induction, in this case with IPTG.

A second strategy used the reaction of the geranyl diphosphate:4-hydroxybenzoate geranyltransferase from *Lithospermum erythrorhizon* (lePGT-1) to divert both isopentenyl diphosphate (IPP) and 4-hydroxybenzoic acid (4-HB) (FIG. 3) away from the production of ubiquinone.

In a previous study, it was demonstrated that lePGT-1 had strict substrate specificity for geranyl diphosphate to form geranyl-4-HB (G-4HB) and was not involved in ubiquinone biosynthesis. The geranyl diphosphate is synthesized from dimethylallyl diphosphate and isopentenyl diphosphate by geranyl diphosphate synthase. This means that 2 mol of isopentenyl diphosphate can convert to 1 mol of geranyl diphosphate.

The reaction catalyzed by lePGT-1 also functions as a competing pathway on the substrates (IPP and 4-HB) of the quinone synthesis pathway. We therefore synthesized lePGT-1 and cloned the gene into two plasmids with different copy numbers (pTrc99a and pBAD33) (FIG. 5A, 5B), and transformed these plasmids into different genetic type E. coli strains to control the quinone synthesis pathway. The 925 bp DNA fragment encoding the geranyl diphosphate:4-hydroxybenzoate geranyltransferase gene from Lithospermum erythrorhizon (lePGT-1) was synthesized and cloned into the vector pTrc99a and pBAD33.

The functionalities of each of these strategies to reduce quinone production leading to an increase in lactate accumulation were successfully demonstrated in aerobic shake flask fermentations (see Table 1-12). The experiments are described in further detail below. Lactate is a typical reductive product, which is usually produced under anaerobic conditions, but it is exemplary only, and other products such as formate, acetate, succinate, 1,2 PDO, ethanol, and the like are also being tested. Lactate is, however, an important chemical, which is used in a wide range of food-processing and pharmaceutical industries. It also can use as the monomer of the biodegradable polylactic acid, which was considered as an environmentally friendly plastic.

Lycopene Diverting Genes

The lycopene synthesis pathway (crtE, crtI, crtB) was introduced in engineered E. coli strains to drain isopentenyl diphosphate (IPP) (FIG. 3) and reduce the activity of the respiratory chain. Two different host strains were applied in this experiment, BW25113 and MG1655. The introduction of these three genes is sufficient for E. coli to produce lycopene from an existing supply of IPP.

These host strains are commonly used for study of metabolic engineering on E. coli. BW25113 (F–, 4(araD-araB) 567, ΔlacZ4787(::rrnB-3), λ⁻, rph-1, Δ(rhaD-rhaB)568, hsdR514) was the original strain for single gene knockout collection, Keio collection. MG1655 (F–, λ⁻, ilvG–, rfb-50, rph-1) is a wild-type E. coli that is well studied. The use of two strains also shows that the strategy is not host strain dependent.

We chose different expressed plasmid systems with different copy number and strength of promoter and combined these in some cases with mutations in the ubiquinone pathway. The genes in the ubiquinone synthesis pathway we chose to use as mutants were not critical for cell growth, but had the effect of reducing the ubiquinone synthesis, thus amplifying the effects of the diversionary pathway. The overexpression plasmid pBAD33 is a low copy number plasmid—we needed to perform this experiment in a background strain with relatively low ubiquinone synthesis in order to clearly demonstrate the effect of the diversionary pathway.

These experiments demonstrate the objective can be attained in a variety of host strains and that a combination of some mutations in a host gene especially in a redundant pathway can adjust the basal level so the diversion or competition strategy for the intermediate works well over the levels of expression of the diverting pathway we employed.

The glucose consumption, lactate production and acetate production from aerobic shake flask fermentation experiments of BW25113 (pAC-LYC), BW25113 ΔubiX, BW25113 ΔubiX (pAC-LYC), BW25113 ΔubiE, BW25113 ΔubiE (pAC-LYC), BW25113 ΔubiG, and BW25113 ΔubiG (pAC-LYC) are shown in Table 1.

The ratio of carbon burnt in each culture was calculated at two time points, one was at the time with highest lactate concentration of the batch process, and the other one was at the end of the batch process. These ratios are shown in Table 2. The results based on MG1655 are shown in Table 3 and 4.

The highest concentrations of reduced product, lactate, in the mutants of BW25113 ΔubiX, BW25113 ΔubiE and BW25113 ΔubiG reached to 48.68, 50.03 and 54.47 mM, respectively. The lactate was re-consumed in the ubiX mutant strain, while it changed little in the other two mutants. A combination of a ubiX mutation and lycopene synthesis pathway overexpression in BW25113, which limited quinone synthesis, directed the carbon flux to reductive product in full aerobic conditions. The theoretical yield of lactate was achieved in BW25113 ΔubiX(pAC-LYC) (around 2 mol/mol glucose). In BW25113 ΔubiE (pAC-LYC) and BW25113 ΔubiG (pAC-LYC), the lactate yields were 1.67 and 1.75 mol/mol glucose, respectively (Table 1). No carbon was burnt aerobically in BW25113 ΔubiX (pAC-LYC), BW25113 ΔubiE (pAC-LYC) and BW25113 ΔubiG (pAC-LYC) (Table 2), while without the plasmid pAC-LYC, only 38.34, 15.07 and 10.9% of the carbon source was burnt during the aerobic culture of BW25113 ΔubiX, BW25113 ΔubiE and BW25113 ΔubiG, respectively (Table 2).

In MG1655, a combination of UbiX mutation (3-octaprenyl-4-hydroxybenzoate decarboxylase) and lycopene synthesis pathway overexpression enhanced the accumulation of lactate from 16.57 mM to 40.67 mM (Table 3). The carbon burnt in cultures of MG1655 ΔubiX (pAC-LYC) at the point of highest lactate concentration was reduced to 11.8%, while in MG1655 (pACYC184) about 37% of carbon was burnt to $CO_2$ (Table 4).

PGT-1 Diverting Gene

The reaction catalyzed by the geranyl diphosphate:4-hydroxybenzoate geranyltransferase from Lithospermum erythrorhizon (lePGT-1) was introduced into the E. coli strains to drain both isopentenyl diphosphate (IPP) and 4-hydroxybenzoic acid (4-HB) (FIG. 3), thus reducing the amount of ubiquinone that can be produced.

Figure 5A:
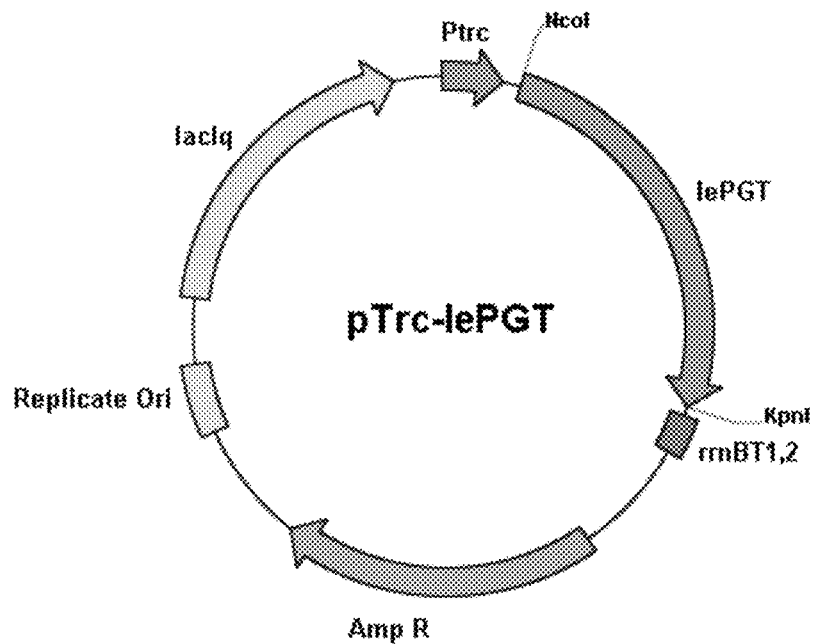
FIG. 5A: pTrc-lePGT.

In this first experiment, lePGT-1 was overexpressed under the trc promoter in pTrc99a, in the constructed plasmid named pTrc-lePGT (FIG. 5A). The pTrc-lePGT was transformed into MG1655. The glucose consumption, lactate production and acetate production from aerobic shake flask fermentation experiments of MG1655 (pTrc-lePGT) using different concentrations of IPTG are shown in Table 5. The ratio of carbon burnt by the culture of the strains was calculated at two time points, one was at the time with highest lactate concentration of the batch process, and the other one was at the end of the batch process, were shown in Table 6.

The phenomena of glucose consumption, lactate and acetate production were similar when 0, 20 and 40 μM concentrations of IPTG were added to induce lePTG expression. The metabolic flux of reduced carbon was highly responsive to induction levels. This was shown when a concentration of more than 40 μM of IPTG was applied in the fully aerobic condition. In the conditions of 40, 60, 80, 100, 200, 500 and 1000 μM of IPTG, the highest concentration of lactate accumulating in the culture increased from around 15 mM to about 66 mM. The concentration of acetate decreased from 130.04 to 63.77 mM. Lactate can be re-consumed when the concentration of IPTG in the culture was below 200 μM.

The carbon burnt was also highly responsive to different induction conditions. From a concentration of 60 to 1000 µM of IPTG, the more IPTG added, the less carbon was burnt during the culture process. When 1000 µM of IPTG was added in the culture medium, only 10.05% of carbon was burnt to $CO_2$ (Table 6).

Figure 6:
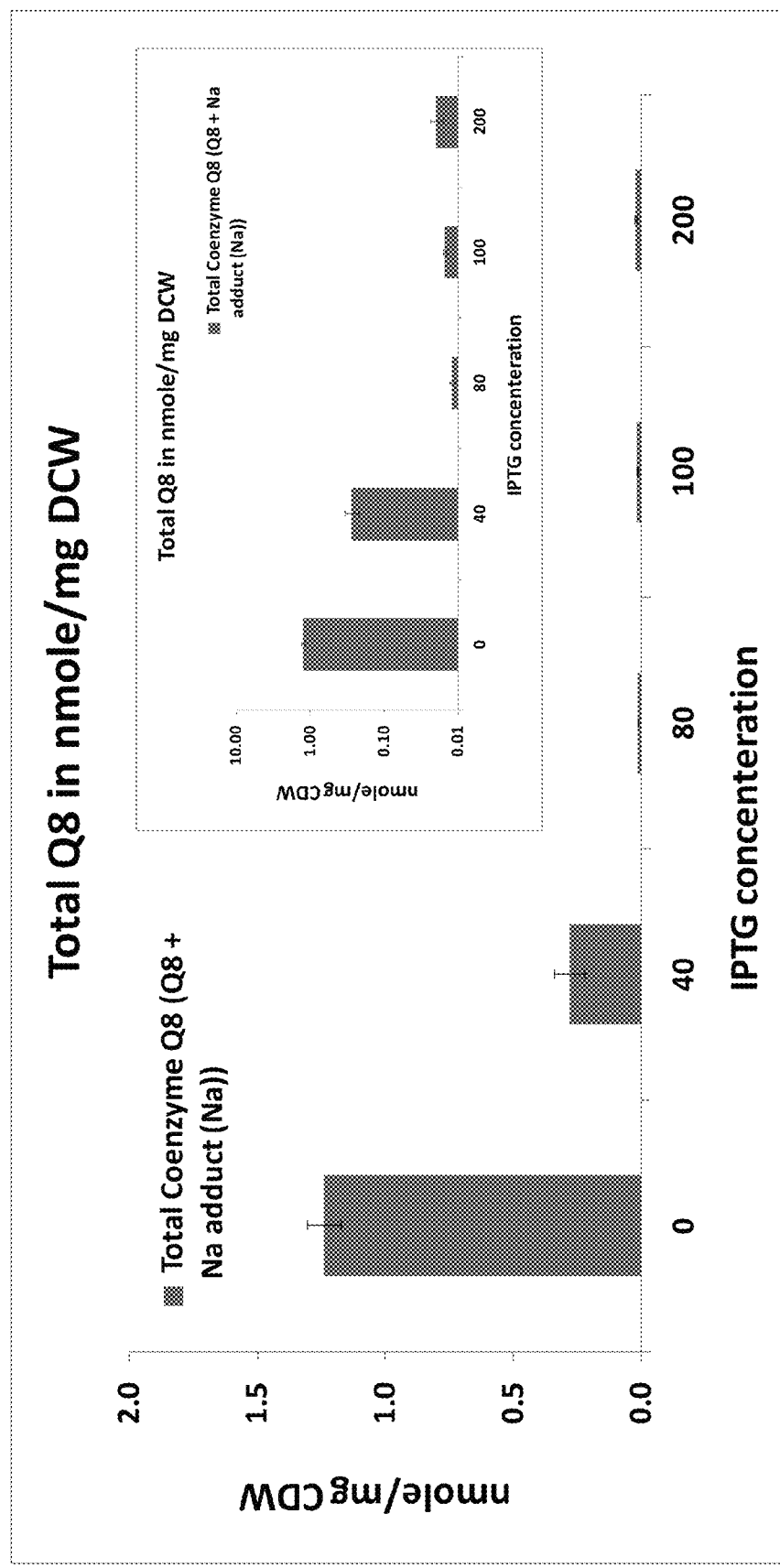
FIG. 6. Coenzyme Q8 concentration (nmol) per mg dry cell weight (DCW) as a function of the inducer, IPTG, concentration (μM).

In addition, preliminary data indicate the coenzyme Q8 concentration also showed a graded response to the inducer IPTG concentration (FIG. 6). Notice that the concentration of coenzyme Q8 (CoQ8) for the wild type strain at 0 µM IPTG is at very low level, only about 1.2 nmole/mg DCW. The CoQ8 concentration dropped by an order of magnitude at higher IPTG concentrations (>80 µM). The concentration at that low concentration level (~10 pmole/mg DCW range) while detectable is below the accuracy of our current experimental protocol. These preliminary data also indicate that further refinement, such as using even more cells, is needed to increase our measuring capability to a higher accuracy at these super low concentrations.

Note that the CoQ8 concentration dropped significantly at 40 µM IPTG when compared with that of 0 µM IPTG (FIG. 6), while the amount of lactate accumulation was very similar (Table 5), suggesting that the wild type strain overproduces CoQ8 under normal aerobic conditions to ensure there is a sufficient quantity of CoQ8 for the ETC system. It is also of interest to note that while the concentration of CoQ8 is very low (FIG. 6), its effect on lactate accumulation is unusually large (in mM range per culture volume) a "gain" of 10,000,000 or 107 when comparing the change in the metabolite being directly controlled by the new node (ubiquinone) to the consequent major pathway (lactate) change.

Figure 5B:
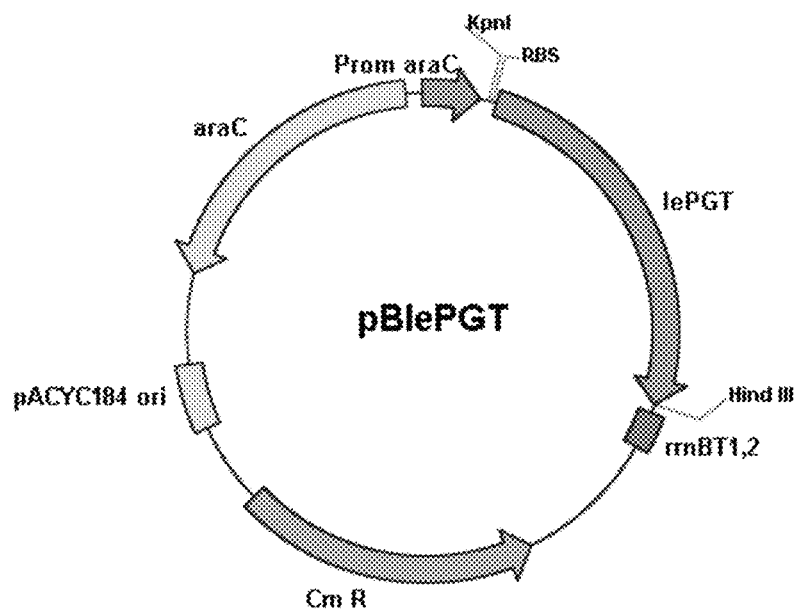
FIG. 5B: pBlePGT. Abbreviations: Ptrc, trc promoter; Prom araC, araC promoter; AmpR, ampicillin resistant gene; CmR, chloramphenicol resistant gene; Replicate Ori, origin of replication; pACYC184 Ori, replication origin of pACYC184; lacIq, lac operon repressor; rrnBT1,2, 1,2 terminators of rrnB; restriction enzyme sites: NocI, KpnI, HindIII.

In a second experiment, lePGT-1 was overexpressed under the arabinose-responsive ara promoter in pBAD33, in the constructed plasmid named pBlePGT (FIG. 5B). The pBlePGT plasmid was transformed into MG1655 ΔubiX, MG1655 ΔubiE and MG1655 ΔubiG.

The glucose consumption, lactate production and acetate production from aerobic shake flask fermentation experiments of MG1655 ΔubiX (pBlePGT), MG1655 ΔubiE (pBlePGT) and MG1655 ΔubiG (pBlePGT) using different concentrations of arabinose are shown in Table 7, 9 and 11, respectively. The ratio of carbon burnt in the cultures of the strains was calculated at two time points, one was at the time with highest lactate concentration of the batch process, and the other one was at the end of the batch process. The results are shown in Table 8, 10, and 12, respectively.

In the experiments of MG1655 ΔubiX (pBlePGT), with concentrations of 0, 0.5, 1, 2, 5, 10, 12, 16, 20 and 50 mM arabinose were investigated (Table 7). The peak value of lactate accumulation during the culture was slightly enhanced, from 28.81 to 32.51 mM, when the concentration of arabinose increased from 0 to 5 mM. The lactate production changed significantly when more arabinose (more than 5 mM) was added to the medium. When concentrations of 10, 12, 16, 20 and 50 mM arabinose were applied, the peak value of the lactate accumulation reached 43.06, 53.07, 68.6, 95.58 and 94.71 mM, respectively. The accumulated lactate can be consumed by the culture in the cases where concentrations of 0, 0.5, 1, 2, 5, 10 and 12 mM arabinose were used, while it became stable or kept increasing in concentrations of 16, 20 and 50 mM arabinose.

The carbon burnt was also highly responsive to different induction conditions. When concentrations of 20 or 50 mM arabinose were added in the medium, almost no carbon was burnt to $CO_2$ (Table 8).

In the experiments using MG1655 ΔubiE (pBlePGT), concentrations of 0, 5, 10, 15 and 20 mM arabinose were investigated (Table 9). The UbiE minus strain with pBAD33 accumulated 64.76 mM of lactate. The induction of pBlePGT further enhanced the lactate production. In the conditions of 0, 5, 10, 15 and 20 mM arabinose, the lactate concentration reached 70.85, 75.23, 82.86, 92.61 and 94.83 mM, respectively.

The concentration of acetate decreased from 55.93 to 14.82 mM. The presence of the ubiE minus mutation in the strain reduced the amount of carbon burnt, to only 16.33%. Further induction of lePGT-1 can reduce the amount of carbon burnt to 0% (Table 10). The lactate yield reached to the anaerobic theoretical yield in the fully aerobic condition with this strain and growth conditions.

In the using of MG1655 ΔubiG (pBlePGT), concentrations of 0, 5, 10, 15 and 20 mM arabinose were investigated (Table 11). Cultures of the UbiG minus strain with pBAD33 accumulated 74.66 mM lactate. The induction of pBlePGT further enhanced the lactate production. In the conditions of 0, 5, 10, 15 and 20 mM arabinose induction of the culture, the lactate concentration reached 77.17, 80.6, 88.97, 93.92 and 92.05 mM, respectively. The concentration of acetate decreased from 50.76 to 10 mM.

In the cultures of UbiG minus strain the amount of carbon burnt, only 3.2%, much lower than the ubiE minus strain. Further induction of lePGT-1 can reduce the amount of carbon burnt to 0%. The lactate yield also reached to the anaerobic theoretical yield in the fully aerobic condition in this strain.

Methods

Aerobic shake flask experiments were performed at 30° C. with shaking at 250 rpm for 48 h with 1% inoculation in 50 ml LB broth medium supplied with 20 g/l glucose, 100 mM phosphate and appropriate quantities of kanamycin, chloramphenicol and ampicillin. The initial pH was 7.0. Different concentrations of IPTG and arabinose were added initially in the media to control the expression of the added genes and/or pathways.

Results

TABLE 1

Metabolite data from aerobic shake flask fermentation experiments of BW25113 (pAC-LYC), BW25113 ΔubiX, BW25113 ΔubiX (pAC-LYC), BW25113 ΔubiE, BW25113 ΔubiE (pAC-LYC), BW25113 ΔubiG, and BW25113 ΔubiG (pAC-LYC).

| | | | Time (h) | | | | |
|---|---|---|---|---|---|---|---|
| Strain | Relevant genotype | Substrate and product | 0 | 3 | 6 | 12 | 24 |
| BW25113 (pAC-LYC) | lyco+ | Glucose consumption | 0.00 | 0.96 | 11.15 | 50.38 | 63.37 |
| BW25113 ΔubiX | ΔubiX | | 0.00 | 0.81 | 8.59 | 46.81 | 60.95 |
| BW25113 ΔubiX (pAC-LYC) | ΔubiX, lyco+ | | 0.00 | 0.81 | 5.15 | 40.57 | 47.61 |
| BW25113 ΔubiE | ΔubiE | | 0.00 | 0.50 | 7.31 | 40.88 | 49.60 |
| BW25113 ΔubiE (pAC-LYC) | ΔubiE, lyco+ | | 0.00 | 0.00 | 6.93 | 39.47 | 47.40 |
| BW25113 ΔubiG | ΔubiG | | 0.00 | 0.058 | 9.55 | 41.95 | 50.37 |

TABLE 1-continued

Metabolite data from aerobic shake flask fermentation experiments of BW25113 (pAC-LYC), BW25113 ΔubiX, BW25113 ΔubiX (pAC-LYC), BW25113 ΔubiE, BW25113 ΔubiE (pAC-LYC), BW25113 ΔubiG, and BW25113 ΔubiG (pAC-LYC).

| Strain | Relevant genotype | Substrate and product | 0 | 3 | 6 | 12 | 24 |
|---|---|---|---|---|---|---|---|
| BW25113 ΔubiG (pAC-LYC) | ΔubiG, lyco+ | | 0.00 | 0.18 | 7.44 | 39.86 | 47.91 |
| BW25113 (pAC-LYC) | lyco+ | Lactate production | 0.00 | 0.081 | 2.00 | 27.00 | 0.0081 |
| BW25113 ΔubiX | ΔubiX | | 0.12 | 0.67 | 10.39 | 48.68 | 0.20 |
| BW25113 ΔubiX (pAC-LYC) | ΔubiX, lyco+ | | 0.00 | 0.50 | 11.75 | 95.69 | 101.50 |
| BW25113 ΔubiE | ΔubiE | | 0.00 | 2.00 | 12.42 | 50.03 | 46.94 |
| BW25113 ΔubiE (pAC-LYC) | ΔubiE, lyco+ | | 0.00 | 2.33 | 15.10 | 69.83 | 79.00 |
| BW25113 ΔubiG | ΔubiG | | 0.00 | 2.26 | 14.30 | 54.36 | 54.47 |
| BW25113 ΔubiG (pAC-LYC) | ΔubiG, lyco+ | | 0.00 | 2.08 | 15.28 | 73.52 | 83.66 |
| BW25113 (pAC-LYC) | lyco+ | Acetate production | 1.33 | 3.56 | 18.52 | 60.24 | 116.33 |
| BW25113 ΔubiX | ΔubiX | | 0.92 | 2.35 | 7.56 | 39.33 | 112.45 |
| BW25113 ΔubiX (pAC-LYC) | ΔubiX, lyco+ | | 1.01 | 2.10 | 3.57 | 6.98 | 17.23 |
| BW25113 ΔubiE | ΔubiE | | 0.80 | 1.16 | 5.65 | 34.66 | 55.95 |
| BW25113 ΔubiE (pAC-LYC) | ΔubiE, lyco+ | | 0.82 | 1.48 | 5.72 | 24.14 | 34.13 |
| BW25113 ΔubiG | ΔubiG | | 0.80 | 1.77 | 8.92 | 34.25 | 52.94 |
| BW25113 ΔubiG (pAC-LYC) | ΔubiG, lyco+ | | 0.00 | 1.38 | 6.17 | 20.07 | 27.01 | lyco+: overexpression of CrtIBE from *Erwinia herbicola* in pACYC184

TABLE 2

The ratio of carbon burnt from aerobic shake flask fermentation experiments of BW25113 (pAC-LYC), BW25113 ΔubiX, BW25113 ΔubiX (pAC-LYC), BW25113 ΔubiE, BW25113 ΔubiE (pAC-LYC), BW25113 ΔubiG, and BW25113 ΔubiG (pAC-LYC).

| Strain | Relevant genotype | Carbon burned[a] at the time point of highest lactate concentration (%) | Carbon burned at the time point of 24 hours (%) |
|---|---|---|---|
| BW25113 (pAC-LYC) | lyco+ | 33.34 | 38.8 |
| BW25113 ΔubiX | ΔubiX | 20.00 | 38.34 |
| BW25113 ΔubiX (pAC-LYC) | ΔubiX, lyco+ | 0.00 | 0.00 |
| BW25113 ΔubiE | ΔubiE | 10.53 | 15.07 |
| BW25113 ΔubiE (pAC-LYC) | ΔubiE, lyco+ | 0.00 | 0.00 |
| BW25113 ΔubiG | ΔubiG | 10.9 | 10.9 |
| BW25113 ΔubiG (pAC-LYC) | ΔubiG, lyco+ | 0.00 | 0.00 | lyco+: overexpression of CrtIBE from *Erwinia herbicola* in pACYC184
[a]Carbon burnt refers to the difference between glucose consumption and metabolite accumulation, which can be attributed to $CO_2$ being released from the culture. Reduced product refers to lactate, ethanol, and succinate, which consume NADH during synthesis

TABLE 3

Metabolite data from aerobic shake flask fermentation experiments of MG1655 (pACYC184), MG1655 (pAC-LYC), MG1655 ΔubiX (pAC-LYC), and MG1655 ΔubiX ΔldhA (pAC-LYC).

| Strain | Relevant genotype | Substrate and product | 0 | 3 | 6 | 9 | 12 | 24 |
|---|---|---|---|---|---|---|---|---|
| MG1655 (pACYC184) | | Glucose consumption | 0.00 | 1.38 | 14.38 | 32.28 | 38.00 | 52.14 |
| MG1655 (pAC-LYC) | lyco+ | | 0.00 | 0.52 | 8.29 | 30.88 | 43.75 | 56.60 |
| MG1655ΔubiX (pAC-LYC) | ΔubiX, lyco+ | | 0.00 | 0.00 | 5.42 | 21.41 | 32.96 | 49.18 |
| MG1655ΔubiX ΔldhA (pAC-LYC) | ΔubiX, ldhA, lyco+ | | 0.00 | 0.070 | 0.31 | 3.67 | 17.25 | 53.46 |
| MG1655 (pACYC184) | | Lactate production | 0.00 | 0.29 | 2.01 | 16.57 | 8.00 | 0.00 |
| MG1655 (pAC-LYC) | lyco+ | | 0.00 | 0.00 | 0.35 | 14.98 | 13.91 | 0.00 |
| MG1655ΔubiX (pAC-LYC) | ΔubiX, lyco+ | | 0.00 | 1.10 | 13.03 | 34.18 | 40.67 | 0.00 |
| MG1655ΔubiX ΔldhA (pAC-LYC) | ΔubiX, ldhA, lyco+ | | 0.00 | 0.00 | 0.00 | 0.00 | 0.00 | 0.00 |
| MG1655 (pACYC184) | | Acetate production | 0.00 | 4.85 | 20.08 | 36.16 | 56.97 | 96.26 |
| MG1655 (pAC-LYC) | lyco+ | | 0.93 | 3.11 | 16.67 | 36.15 | 56.44 | 108.23 |
| MG1655ΔubiX (pAC-LYC) | ΔubiX, lyco+ | | 0.00 | 1.51 | 4.54 | 14.16 | 26.22 | 92.62 |
| MG1655ΔubiX ΔldhA (pAC-LYC) | ΔubiX, ldhA, lyco+ | | 0.00 | 1.51 | 2.04 | 5.68 | 22.06 | 94.91 | lyco+: overexpression of CrtIBE from *Erwinia herbicola* in pACYC184

TABLE 4

The ratio of carbon burnt from aerobic shake flask fermentation experiments of MG1655 (pACYC184), MG1655 (pAC-LYC), MG1655ΔubiX (pAC-LYC), and MG1655ΔubiXΔldhA (pAC-LYC) at 24 hours.

| Strain | Relevant genotype | Carbon burned at the time point of highest lactate concentration (%) | Carbon burned at the time point of 24 hours (%) |
|---|---|---|---|
| MG1655 (pACYC184) | | 37.00 | 38.46 |
| MG1655 (pAC-LYC) | lyco+ | 36.71 | 36.26 |
| MG1655ΔubiX (pAC-LYC) | ΔubiX, lyco+ | 11.80 | 37.22 |
| MG1655ΔubiXΔldhA (pAC-LYC) | ΔubiX, ldhA, lyco+ | 40.82 | 40.82 | lyco+: overexpression of CrtIBE from *Erwinia herbicola* in pACYC184

TABLE 6

The ratio of carbon burnt from aerobic shake flask fermentation experiments of MG1655 (pTrc-lePGT) in different IPTG concentration.

| Strain | Relevant genotype | IPGT (μm) | Carbon burned[a] at the time point of highest lactate concentration (%) | Carbon burned at the time point of 48 hours (%) |
|---|---|---|---|---|
| MG1655 (pTrc-lePGT) | PGT-1+ | 0 | 33.99 | 35.70 |
| | | 20 | 31.81 | 33.59 |
| | | 40 | 32.92 | 34.13 |
| | | 60 | 33.84 | 34.25 |
| | | 80 | 18.66 | 32.01 |
| | | 100 | 10.44 | 24.24 |
| | | 200 | 11.72 | 11.72 |
| | | 500 | 10.19 | 10.19 |
| | | 1000 | 10.05 | 10.05 |

PGT-1+: overexpression of geranyl diphosphate: 4-hydroxybenzoate 3-geranyltransferase from *Lithospermum erythrorhizon* in pTrc99A.
[a]Carbon burnt refers to the difference between glucose consumption and metabolite accumulation, which can be attributed to $CO_2$ released from the culture. Reduced product refers to lactate, ethanol, and succinate, which consume NADH during synthesis.

TABLE 5

Metabolite data from aerobic shake flask fermentation experiments of MG1655 (pTrc-lePGT) in different concentrations of IPTG.

| Strain | Relevant genotype | IPGT (μm) | Substrate and product | Time (h) | | | | | | | | | |
|---|---|---|---|---|---|---|---|---|---|---|---|---|---|
| | | | | 0 | 3 | 6 | 9 | 12 | 15 | 24 | 30 | 36 | 48 |
| MG1655 (pTrc-lePGT) | PGT-1+ | 0 | Glucose consumption | 0.00 | 0.29 | 7.15 | 24.51 | 34.19 | 43.82 | 53.68 | 58.68 | 61.86 | 67.81 |
| | | 20 | | 0.00 | 0.00 | 6.91 | 22.86 | 32.93 | 41.54 | 51.43 | 56.23 | 59.68 | 64.56 |
| | | 40 | | 0.00 | 0.41 | 6.74 | 22.64 | 34.21 | 41.14 | 52.20 | 56.07 | 60.37 | 66.00 |
| | | 60 | | 0.00 | 0.55 | 3.82 | 19.37 | 39.44 | 45.64 | 53.71 | 58.63 | 63.20 | 69.28 |
| | | 80 | | 0.00 | 0.63 | 3.23 | 19.38 | 3.00 | 46.36 | 52.94 | 57.26 | 62.21 | 68.54 |
| | | 100 | | 0.00 | 0.68 | 3.10 | 20.18 | 38.21 | 46.50 | 52.63 | 56.39 | 60.96 | 68.26 |
| | | 200 | | 0.00 | 2.76 | 5.88 | 24.76 | 38.09 | 45.20 | 50.32 | 53.98 | 57.30 | 61.02 |
| | | 500 | | 0.00 | 1.58 | 5.88 | 19.91 | 38.62 | 44.68 | 50.79 | 54.04 | 56.87 | 60.56 |
| | | 1000 | | 0.00 | 1.83 | 5.53 | 19.84 | 38.36 | 44.24 | 50.50 | 53.93 | 56.54 | 60.19 |
| MG1655 (pTrc-lePGT) | PGT-1+ | 0 | Lactate production | 0.00 | 0.074 | 0.38 | 6.75 | 15.06 | 3.65 | 0.00 | 0.00 | 0.00 | 0.00 |
| | | 20 | | 0.00 | 0.00 | 0.20 | 5.81 | 13.58 | 3.61 | 0.00 | 0.00 | 0.00 | 0.00 |
| | | 40 | | 0.00 | 0.00 | 0.00 | 5.00 | 15.09 | 5.65 | 0.00 | 0.00 | 0.00 | 0.00 |
| | | 60 | | 0.00 | 0.00 | 0.6 | 6.77 | 25.78 | 25.27 | 1.36 | 0.00 | 0.00 | 0.00 |
| | | 80 | | 0.00 | 0.00 | 0.86 | 10.97 | 37.79 | 39.79 | 17.51 | 8.71 | 4.08 | 4.50 |
| | | 100 | | 0.00 | 0.00 | 1.08 | 14.94 | 48.39 | 51.82 | 35.2 | 28.54 | 26.97 | 30.04 |
| | | 200 | | 0.00 | 0.00 | 1.28 | 19.95 | 53.33 | 55.72 | 55.6 | 57.46 | 58.44 | 64.54 |
| | | 500 | | 0.00 | 0.00 | 1.04 | 20.96 | 52.94 | 56.54 | 57.49 | 59.16 | 60.94 | 66.1 |
| | | 1000 | | 0.00 | 0.00 | 0.38 | 21.01 | 53.11 | 58.17 | 58.24 | 59.48 | 60.5 | 65.77 |
| MG1655 (pTrc-lePGT) | PGT-1+ | 0 | Acetate production | 0.00 | 2.12 | 10.27 | 29.67 | 45.1 | 67.12 | 97.74 | 107.25 | 114.31 | 130.79 |
| | | 20 | | 0.00 | 2.29 | 11.05 | 30.1 | 46.99 | 66.00 | 96.09 | 105.33 | 112.15 | 128.62 |
| | | 40 | | 0.00 | 0.5 | 10.4 | 29.15 | 46.20 | 64.43 | 93.41 | 104.81 | 112.55 | 130.4 |
| | | 60 | | 0.00 | 2.14 | 8.64 | 25.65 | 39.60 | 58.79 | 102.66 | 113.26 | 119.83 | 136.65 |
| | | 80 | | 0.00 | 2.05 | 5.39 | 24.21 | 37.24 | 53.45 | 87.68 | 105.40 | 115.20 | 133.06 |
| | | 100 | | 0.00 | 1.91 | 8.01 | 21.67 | 33.97 | 47.22 | 75.21 | 88.92 | 97.09 | 110.08 |
| | | 200 | | 0.00 | 2.28 | 8.01 | 14.96 | 28.93 | 35.65 | 49.62 | 55.38 | 59.25 | 64.79 |
| | | 500 | | 0.00 | 0.00 | 6.99 | 18.24 | 27.50 | 34.90 | 48.29 | 53.98 | 58.01 | 64.01 |
| | | 1000 | | 0.00 | 2.04 | 7.09 | 18.15 | 27.21 | 34.65 | 47.84 | 53.24 | 58.00 | 63.77 |

PGT-1+: overexpression of geranyl diphosphate: 4-hydroxybenzoate 3-geranyltransferase from *Lithospermum erythrorhizon* in pTrc99A.

TABLE 7

Metabolite data from aerobic shake flask fermentation experiments of MG1655 ΔubiX (pBlePGT) in different concentrations of arabinose.

| Strain | Relevant genotype | Arabinose (mM) | Substrate and product | Time (h) 0 | 3 | 6 | 9 | 12 | 15 | 24 | 30 | 36 | 48 |
|---|---|---|---|---|---|---|---|---|---|---|---|---|---|
| MG1655ΔubiX, (pBlePGT) | ΔubiX, PGT-1+ | 0 | Glucose consumption | 0.00 | 3.01 | 7.84 | 18.14 | 30.86 | 35.69 | 49.22 | 49.78 | 57.01 | 61.7 |
| | | 0.5 | | 0.00 | 0.54 | 6.17 | 18.23 | 29.52 | 33.96 | 47.74 | 51.02 | 53.85 | 60.6 |
| | | 1 | | 0.00 | 0.23 | 6.13 | 17.27 | 30.25 | 34.53 | 47.25 | 51.16 | 55.77 | 59.5 |
| | | 2 | | 0.00 | 0.00 | 3.48 | 16.82 | 30.18 | 34.15 | 47.00 | 51.28 | 54.6 | 59.89 |
| | | 5 | | 0.00 | 0.00 | 2.61 | 16.9 | 30.37 | 34.87 | 47.00 | 51.02 | 55.26 | 59.81 |
| | | 10 | | 0.00 | 0.71 | 4.14 | 19.24 | 35.4 | 41.81 | 45.73 | 52.28 | 57.29 | 61.51 |
| | | 12 | | 0.00 | 0.028 | 4.14 | 20.44 | 35.94 | 41.61 | 47.89 | 50.42 | 54.24 | 59.51 |
| | | 16 | | 0.00 | 0.69 | 3.53 | 22.39 | 39.09 | 42.79 | 48.47 | 52 | 55.35 | 57.81 |
| | | 20 | | 0.00 | 0.00 | 1.95 | 21.46 | 36.15 | 38.65 | 44.13 | 45.81 | 48.03 | 49.7 |
| | | 50 | | 0.00 | 0.64 | 6.4 | 19.72 | 35.95 | 37.41 | 42.8 | 43.11 | 45.16 | 46.43 |
| MG1655ΔubiX, (pBlePGT) | ΔubiX, PGT-1+ | 0 | Lactate production | 0.00 | 0.35 | 7.4 | 22.14 | 28.81 | 19.67 | 0.00 | 0.00 | 0.00 | 0.00 |
| | | 0.5 | | 0.00 | 0.3 | 7.75 | 22.14 | 29.4 | 18.87 | 0.00 | 0.00 | 0.00 | 0.00 |
| | | 1 | | 0.00 | 0.26 | 7.57 | 22.08 | 28.33 | 21.22 | 0.00 | 0.00 | 0.00 | 0.00 |
| | | 2 | | 0.00 | 0.25 | 7.17 | 22.19 | 30.96 | 21.2 | 0.00 | 0.00 | 0.00 | 0.00 |
| | | 5 | | 0.00 | 0.34 | 7.36 | 22.9 | 32.51 | 22.24 | 0.00 | 0.00 | 0.00 | 0.00 |
| | | 10 | | 0.00 | 0.00 | 6.93 | 25.81 | 43.06 | 42.12 | 3.69 | 0.00 | 0.00 | 0.00 |
| | | 12 | | 0.00 | 0.00 | 5.36 | 28.4 | 51.86 | 53.07 | 33.018 | 22.25 | 16.07 | 11.97 |
| | | 16 | | 0.00 | 0.00 | 5.51 | 35.83 | 64.09 | 66.29 | 64.45 | 65.31 | 66.3 | 68.6 |
| | | 20 | | 0.00 | 0.00 | 7.3 | 44.79 | 76.32 | 79.11 | 85.22 | 89.26 | 91.26 | 95.58 |
| | | 50 | | 0.00 | 0.00 | 7.28 | 42.65 | 79.11 | 83.04 | 86.34 | 90.02 | 91.04 | 94.71 |
| MG1655ΔubiX, (pBlePGT) | ΔubiX, PGT-1+ | 0 | Acetate production | 0.82 | 1.61 | 4.50 | 14.43 | 26.80 | 40.42 | 86.66 | 95.95 | 99.77 | 116.65 |
| | | 0.5 | | 0.00 | 1.40 | 4.77 | 14.68 | 26.92 | 40.88 | 87.08 | 96.63 | 102.78 | 118.21 |
| | | 1 | | 0.00 | 1.58 | 4.66 | 14.52 | 26.98 | 41.13 | 87.52 | 96.99 | 103.48 | 119.41 |
| | | 2 | | 0.00 | 1.47 | 4.57 | 14.41 | 26.88 | 41.53 | 87.40 | 96.85 | 101.44 | 119.51 |
| | | 5 | | 0.00 | 1.44 | 4.36 | 14.42 | 26.65 | 40.56 | 87.51 | 97.12 | 99.60 | 119.12 |
| | | 10 | | 0.00 | 1.53 | 4.47 | 13.46 | 24.37 | 38.39 | 80.60 | 100.02 | 104.58 | 124.94 |
| | | 12 | | 0.00 | 1.03 | 4.24 | 13.10 | 21.85 | 33.32 | 59.09 | 74.51 | 84.96 | 104.84 |
| | | 16 | | 0.00 | 1.27 | 4.17 | 11.62 | 19.14 | 22.62 | 36.02 | 41.92 | 46.01 | 52.93 |
| | | 20 | | 0.00 | 1.54 | 4.24 | 9.47 | 14.30 | 16.04 | 20.84 | 23.53 | 25.33 | 28.85 |
| | | 50 | | 0.00 | 1.50 | 3.79 | 6.43 | 8.71 | 9.57 | 10.79 | 11.95 | 12.35 | 13.12 |

PGT-1+: overexpression of geranyl diphosphate: 4-hydroxybenzoate 3-geranyltransferase from *Lithospermum erythrorhizon* in pBAD33 which is under the control of the arabinose inducible promoter.

TABLE 8

The ratio of carbon burnt from aerobic shake flask fermentation experiments of MG1655 ΔubiX (pBlePGT) in different IPTG concentrations at the time point of highest lactate concentration.

| Strain | Relevant genotype | Arabinose (mM) | Carbon burned[a] at the time point of highest lactate concentration (%) | Carbon burned at the time point of 48 hours (%) |
|---|---|---|---|---|
| MG1655ΔubiX (pBlePGT) | ΔubiX, PGT-1+ | 0 | 24.36 | 36.99 |
| | | 0.5 | 19.79 | 34.97 |
| | | 1 | 23.44 | 33.10 |
| | | 2 | 19.01 | 33.48 |
| | | 5 | 17.23 | 33.61 |
| | | 10 | 16.23 | 32.29 |
| | | 12 | 9.54 | 31.22 |
| | | 16 | 10.16 | 10.16 |
| | | 20 | 0.00 | 0.00 |
| | | 50 | 0.00 | 0.00 |

PGT-1+: overexpression of geranyl diphosphate: 4-hydroxybenzoate 3-geranyltransferase from *Lithospermum erythrorhizon* in pBAD33.
[a]Carbon burnt refers to the difference between glucose consumption and metabolite accumulation, which can be attributed to CO2 released from the culture. Reduced product refers to lactate, ethanol, and succinate, which consume NADH during synthesis.

TABLE 9

Metabolite data from aerobic shake flask fermentation experiments of MG1655 ΔubiE (pBlePGT) in different concentrations of arabinose.

| Strain | Relevant genotype | Arabinose (mM) | Substrate and product | Time (h) 0 | 6 | 9 | 12 | 15 | 24 | 30 | 36 | 48 |
|---|---|---|---|---|---|---|---|---|---|---|---|---|
| MG1655 ΔubiE, (pBAD33) | ΔubiE | | Glucose consumption | 0.00 | 1.15 | 8.05 | 18.85 | 37.35 | 48.51 | 52.00 | 57.17 | 62.38 |
| MG1655ΔubiE, (pBlePGT) | ΔubiE, PGT-1+ | 0 | | 0.00 | 2.98 | 6.72 | 11.53 | 28.57 | 48.20 | 52.51 | 57.14 | 60.22 |
| | | 5 | | 0.00 | 0.85 | 5.15 | 9.12 | 29.32 | 48.04 | 52.09 | 55.83 | 58.49 |
| | | 10 | | 0.00 | 1.15 | 5.07 | 9.37 | 31.03 | 47.73 | 51.37 | 53.90 | 55.05 |

TABLE 9-continued

Metabolite data from aerobic shake flask fermentation experiments of MG1655 ΔubiE (pBlePGT) in different concentrations of arabinose.

| Strain | Relevant genotype | Arabinose (mM) | Substrate and product | Time (h) | | | | | | | | |
|---|---|---|---|---|---|---|---|---|---|---|---|---|
| | | | | 0 | 6 | 9 | 12 | 15 | 24 | 30 | 36 | 48 |
| | | 15 | | 0.00 | 3.31 | 5.02 | 9.81 | 29.02 | 44.97 | 48.18 | 50.63 | 52.28 |
| | | 20 | | 0.00 | 2.77 | 5.56 | 8.51 | 24.85 | 43.17 | 46.99 | 48.75 | 49.97 |
| MG1655ΔubiE, (pBAD33) | ΔubiE | | Lactate production | 0.00 | 1.07 | 5.99 | 23.73 | 47.84 | 52.17 | 54.07 | 57.51 | 64.76 |
| MG1655ΔubiE, (pBlePGT) | ΔubiE, PGT-1+ | 0 | | 0.00 | 0.91 | 3.58 | 13.87 | 39.51 | 57.33 | 59.09 | 61.50 | 70.85 |
| | | 5 | | 0.00 | 0.80 | 3.41 | 13.56 | 41.04 | 61.14 | 64.53 | 67.53 | 75.23 |
| | | 10 | | 0.00 | 0.81 | 3.33 | 13.75 | 48.84 | 71.00 | 73.45 | 77.43 | 82.86 |
| | | 15 | | 0.00 | 0.70 | 3.04 | 12.34 | 50.67 | 82.02 | 84.73 | 86.78 | 92.61 |
| | | 20 | | 0.00 | 0.69 | 2.88 | 10.94 | 41.08 | 85.19 | 87.14 | 88.91 | 94.83 |
| MG1655ΔubiE, (pBAD33) | ΔubiE | | Acetate production | 0.00 | 1.00 | 2.34 | 8.75 | 20.94 | 44.03 | 50.82 | 54.59 | 59.44 |
| MG1655ΔubiE, (pBlePGT) | ΔubiE, PGT-1+ | 0 | | 0.00 | 0.78 | 1.67 | 4.39 | 14.39 | 40.23 | 45.97 | 50.72 | 55.93 |
| | | 5 | | 0.00 | 0.92 | 1.74 | 4.17 | 13.24 | 36.02 | 40.69 | 44.86 | 48.53 |
| | | 10 | | 0.00 | 1.00 | 1.61 | 3.95 | 11.42 | 27.64 | 30.77 | 33.14 | 36.18 |
| | | 15 | | 0.00 | 1.03 | 1.59 | 3.09 | 6.56 | 15.41 | 17.35 | 18.48 | 19.75 |
| | | 20 | | 0.00 | 1.02 | 1.44 | 2.59 | 4.28 | 11.02 | 12.45 | 13.66 | 14.82 |

PGT-1+: overexpression of geranyl diphosphate: 4-hydroxybenzoate 3-geranyltransferase from *Lithospermum erythrorhizon* in pBAD33.

TABLE 10

The ratio of carbon burnt[a] from aerobic shake flask fermentation experiments of MG1655 ΔubiE (pBlePGT) in different IPTG concentrations at the time point of highest lactate concentration.

| Strain | Relevant genotype | Arabinose (mM) | Carbon burned[a] at the time point of highest lactate concentration (%) | Carbon burned at the time point of 48 hours (%) |
|---|---|---|---|---|
| MG1655 ΔubiE (pBAD33) | ΔubiE | | 16.33 | 16.33 |
| MG1655ΔubiE, (pBlePGT) | ΔubiE, PGT-1+ | 0 | 10.21 | 10.21 |
| | | 5 | 8.03 | 8.03 |
| | | 10 | 2.83 | 2.83 |
| | | 15 | 0.00 | 0.00 |
| | | 20 | 0.00 | 0.00 |

PGT-1+: overexpression of geranyl diphosphate: 4-hydroxybenzoate 3-geranyltransferase from *Lithospermum erythrorhizon* in pBAD33.
[a]Carbon burnt refers to the difference between glucose consumption and metabolite accumulation, which can be attributed to CO2 released from the culture. Reduced product refers to lactate, ethanol, and succinate, which consume NADH during synthesis.

TABLE 11

Metabolite data from aerobic shake flask fermentation experiments of MG1655 ΔubiG (pBlePGT) in different concentrations of arabinose.

| Strain | Relevant genotype | Arabinose (mM) | Substrate and product | Time (h) | | | | | | | | |
|---|---|---|---|---|---|---|---|---|---|---|---|---|
| | | | | 0 | 12 | 15 | 18 | 21 | 24 | 27 | 36 | 48 |
| MG1655 ΔubiG, (pBAD33) | ΔubiG | | Glucose consumption | 0.00 | 9.37 | 11.77 | 32.38 | 39.67 | 44.87 | 46.78 | 50.56 | 55.96 |
| MG1655ΔubiG, (pBlePGT) | ΔubiG, PGT-1+ | 0 | | 0.00 | 7.74 | 17.56 | 36.47 | 42.36 | 45.46 | 46.54 | 51.28 | 56.51 |
| | | 5 | | 0.00 | 0.00 | 14.40 | 35.58 | 41.46 | 43.75 | 44.42 | 49.78 | 54.38 |
| | | 10 | | 0.00 | 0.59 | 13.79 | 36.66 | 40.98 | 43.19 | 44.15 | 47.74 | 51.05 |
| | | 15 | | 0.00 | 0.61 | 7.12 | 34.08 | 39.38 | 41.57 | 42.54 | 45.26 | 48.10 |
| | | 20 | | 0.00 | 1.77 | 4.96 | 25.42 | 39.67 | 41.05 | 41.99 | 45.06 | 47.19 |
| MG1655ΔubiG, (pBAD33) | ΔubiG | | Lactate production | 0.00 | 7.38 | 26.44 | 51.19 | 60.03 | 60.28 | 61.06 | 68.11 | 74.66 |
| MG1655ΔubiG, (pBlePGT) | ΔubiG, PGT-1+ | 0 | | 0.00 | 9.27 | 33.10 | 57.32 | 61.47 | 61.72 | 64.16 | 70.11 | 77.17 |
| | | 5 | | 0.00 | 8.76 | 30.53 | 58.63 | 63.87 | 64.81 | 67.95 | 73.84 | 80.60 |
| | | 10 | | 0.00 | 7.86 | 31.76 | 69.91 | 73.28 | 75.03 | 78.18 | 84.02 | 88.97 |
| | | 15 | | 0.00 | 6.23 | 22.41 | 69.44 | 80.09 | 81.99 | 83.98 | 88.83 | 93.92 |
| | | 20 | | 0.00 | 4.87 | 15.94 | 45.99 | 78.09 | 81.94 | 84.53 | 87.84 | 92.05 |
| MG1655ΔubiG, (pBAD33) | ΔubiG | | Acetate production | 0.00 | 2.71 | 7.41 | 17.82 | 29.14 | 34.36 | 38.27 | 45.56 | 50.52 |

TABLE 11-continued

Metabolite data from aerobic shake flask fermentation experiments of MG1655 ΔubiG (pBlePGT) in different concentrations of arabinose.

| Strain | Relevant genotype | Arabinose (mM) | Substrate and product | 0 | 12 | 15 | 18 | 21 | 24 | 27 | 36 | 48 |
|---|---|---|---|---|---|---|---|---|---|---|---|---|
| MG1655ΔubiG, (pBlePGT) | ΔubiG, PGT-1+ | 0 | | 0.00 | 2.78 | 10.32 | 21.89 | 30.85 | 35.54 | 39.20 | 46.23 | 50.76 |
| | | 5 | | 0.00 | 2.68 | 7.75 | 19.60 | 28.20 | 32.49 | 35.38 | 41.28 | 45.45 |
| | | 10 | | 0.00 | 2.35 | 7.58 | 15.15 | 20.56 | 23.56 | 25.51 | 29.50 | 32.15 |
| | | 15 | | 0.00 | 1.82 | 3.23 | 6.33 | 8.92 | 10.31 | 11.02 | 12.60 | 13.82 |
| | | 20 | | 0.00 | 1.52 | 2.58 | 3.68 | 5.93 | 7.14 | 7.87 | 9.50 | 10.00 |

PGT-1+: overexpression of geranyl diphosphate: 4-hydroxybenzoate 3-geranyltransferase from *Lithospermum erythrorhizon* in pBAD33.

TABLE 12

The ratio of carbon burnt from aerobic shake flask fermentation experiments of MG1655 ΔubiG (pBlePGT) at different IPTG concentrations at the time point of highest lactate concentration.

| Strain | Relevant genotype | Arabinose (mM) | Carbon burned[a] at the time point of highest lactate concentration (%) | Carbon burned at the time point of 48 hours (%) |
|---|---|---|---|---|
| MG1655 ΔubiG, (pBAD33) | ΔubiG | | 3.20 | 3.20 |
| MG1655ΔubiG, (pBlePGT) | ΔubiG, PGT-1+ | 0 | 1.78 | 1.78 |
| | | 5 | 0.00 | 0.00 |
| | | 10 | 0.00 | 0.00 |
| | | 15 | 0.00 | 0.00 |
| | | 20 | 0.00 | 0.00 |

PGT-1+: overexpression of geranyl diphosphate: 4-hydroxybenzoate 3-geranyltransferase from *Lithospermum erythrorhizon* in pBAD33.
[a]Carbon burnt refers to the difference between glucose consumption and metabolite accumulation, which can be attributed to CO2 released from the culture. Reduced product refers to lactate, ethanol, and succinate, which consumes NADH during synthesis.

Biotin Diversion to Increase Glutamate

*Corynebacterium glutamicum* is a biotin auxotrophic Gram-positive bacterium that is used for large-scale production of amino acids, especially of L-glutamate and L-lysine. It is already known that biotin limitation triggers L-glutamate production (Peters-Wendisch, 2012). The inventive method could therefore be used to limit biotin availability in the host and thus increase glutamate production.

Biotin-CoA ligase aka biotin CoA synthetase [E.C. 6.2.1.11] catalyzes the following reaction:

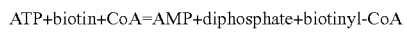

ATP+biotin+CoA=AMP+diphosphate+biotinyl-CoA

Cloning and overexpressing biotin coA synthetase (e.g. YP_004681889; YP_841268.1; AEI80656.1; CAJ96538.1) will thus reduce the level of biotin for forming active carboxylating enzymes, thus leading to increased glutamate production.

Folate Diversion to Increase Serine

In the case of serine production by *Corynebacterium glutamicum*, the reduction of folate allows higher production of serine (Stolz, 2007). Folate availability can be reduced by diversion of biosynthetic intermediates. For example 4-aminobenzoate is needed in the synthesis of 7,8-dihydropteroate—a precursor of folate. This could be depleted by overexpression of 4-aminobenzoate 1-monooxygenase [E.C.1.14.13.27] or aminobenzoate decarboxylase [E.C. 4.1.1.24] and thus depleting the level of the intermediate 4-aminobenzoate. Either enzyme could be overexpressed and deplete the availability of this precursor and reduce the level of activity of the folate compounds with the consequences of increased serine production.

Pantothenate Diversion to Increase Valine

In this example the biosynthesis of pantothenate, a precursor of coenzyme A, can be reduced by diversion and this will lead to flow of metabolism to the precursors of valine, resulting in increased valine production. The level of pantothenate can be reduced by overexpression of the enzyme a pantothenate hydrolyase [E.C. 3.5.1.22]. The effects of reduced pantothenate were examined in Blombach (2007), and increased valine was observed.

There are many other ways to induce a shift away from aerobic respiration towards anaerobic pathways, and thus increase the production of products such as lactate, succinate and the like. In the experiments above, this was demonstrated using lycopene diverting genes as well as the PGT gene to divert precursors away from ubiquinone production, thus slowing the ETC. However, there are other cofactors that can be targeted in the same pathway. The following examples describe some of these additional methods.

Heme Diversion

Another targetable cofactor in the ETC is the heme normally required to reduce cytochrome oxidase activity and allow aerobic respiration.

In aerobic respiration, cytochrome proteins play an essential role as terminal oxidases with Cyo and Cyd being dominant at high oxygen and low oxygen levels, respectively (Borisov et al, 2011; Thony-Meyer, 1997). Heme synthesis and incorporation are important in production of functional cytochromes and in efforts to overproduce heme-containing proteins in *E. coli* where difficulties have often been encountered (Londer, 2011; Tsai et al, 2000; Varnado et al, 2013). The biosynthetic pathway of heme has been determined and enzymes and genes are known.

Heme deficient mutants do not consume oxygen and form lactate as the main fermentation product from glucose (Schellhorn & Hassan, 1988). At a branch the pathway is connected to the formation of siroheme via CysG, uroporphyrinogen III methylase (Spencer et al, 1993; Warren et al, 1994; Warren et al, 1990). This reaction branches from uroporphyrinogen III to siroheme while that catalyzed by HemE proceeds along the heme biosynthetic pathway via HemeNGH to protoheme IX and on to form heme o and heme d, the prosthetic groups of cytochrome o oxidase and cytochrome d oxidase.

This arrangement of the metabolic pathway suggests that overexpression of cysG could divert substrate from the pathway and reduce the level of heme for the respiratory cytochrome oxidases and thereby limit respiration. In preliminary experiments to prove this, we have observed a reduction of aerobic growth of cysG overexpressing cells where cysG is overexpressed from plasmid under control of a lac-controlled promoter (see FIG. 7). This is particularly evident in hemN or hemF background strains where heme synthesis is lowered by mutation of one of these redundant pathway genes and smaller colonies were seen on plates where cysG was partially induced. Increased lactate was also observed (see FIG. 8).

Thiamine Diversion

Another route to achieve divert carbons towards the products of anaerobic metabolism, is to limit the availability of thiamine-needed for aerobic pyruvate dehydrogenase (PDH) formation (Taboada, 2008). This would allow us to make products derived from pyruvate, such as lactate, alanine, butane diol and the like, and acetolactate derived products, such as branched chain amino acids and the like. Precursors of thiamine could be diverted to reduce the availability of subsequent thiamine precursors or by introducing a degradative enzyme of thiamine, such as thiamine pyridinylase [EC:2.5.1.2] or the enzyme aminopyrimidine aminohydrolase [E.C. 3.5.99.2] catalyzing the hydrolysis of thiamine.

Lipoic Acid Diversion

The reduction of lipoate would also be expected to result in a shift toward more lactate, indicative of a loss in ability to perform aerobic respiration, as has been observed in mutants where the pyruvate dehydrogenase (PDH) is completely knocked out and non-functional.

Very little lipoic acid is needed by cells. Analysis of lipoate biosynthetic mutants showed that lipB mutants have reduced PDH activity and reduced alpha ketoglutarate dehydrogenase (KGDH) activity and had about a 10 fold reduction in protein bound lipoic acid and free lipoic acid (Reed & Cronan, 1993). The levels of LipA and LipB are below the limits of proteomic analyses (300 molecules/cell) (Hassan & Cronan, 2011; Lu et al, 2007) and PDH complexes can retain full enzymatic activity despite containing E2 proteins that have only partial lipoylation and either lack lipoyl domains or contain some lipoyl domains that cannot be modified (Perham, 1991).

The PDH activity of the lipB deletion strain ZX221 is about 4% of wild type and it is unable to grow aerobically on glucose minimal medium without supplementation with lipoic acid, octanoic acid or succinate and acetate (Hermes & Cronan, 2009). The overproduction of LplA protein, a protein that can use free octanoic acid as substrate, or high affinity mutants of LplA can allow growth of lipB mutants by using octanoic acid (naturally present in cells at a concentration of 28 micromolar) as a precursor of lipoate (Hermes & Cronan, 2009; Morris et al, 1995).

If a diverting gene is added to the cell that can utilize the octanoate at an appropriately low level, e.g. the fatty acid degradation system, this would be expected to reduce the level of this needed substrate for LplA and reduce the amount of functional PDH containing its essential lipoate prosthetic group. We could employ the genes of the fatty acid degradation system (e.g. fadD of *E. coli* expressed at varying levels, or if not sufficient, the more efficient enzymes form *Salmonella enterica*) (Iram & Cronan, 2006). The Km of *E. coli* acyl-CoA synthase on octanoic acid is reported between 6 and 40 micromolar, near the estimated concentration of octanoic acid in normal cells, (Kameda & Imai, 1985) and below that of the Km of normal LplA (Hermes & Cronan, 2009).

The base strain would be ZX221 (Hermes & Cronan, 2009) or equivalent, and the fad system, fadD the fatty acid acyl-CoA synthase, would be cloned and expressed on a low copy number vector to create a diverting pathway to reduce lipase levels. Alternatively, its expression could be altered in the chromosome by using a fadR mutant to deregulate its expression or introducing a modified set of promoters to replace the fadD natural promoter within the chromosome to create a library of strains with different expression levels of fadD to reduce the level of octanoic acid in the cell. Methods for analysis of those low levels of octanoic acid have been described (Hermes & Cronan, 2009).

It is expected that modifying the level of fadD will divert lipoic acid, thus decreasing the levels of active PDH, and allowing increased production of lactate, and other products produced by fermentation.

Inhibitor Diversion to Increase Tyr & Phe

Another way of affecting metabolism via diversion of a metabolite is through the removal of a feedback process, e.g. reducing the level of a metabolite that has a negative feedback on a pathway via inhibition of an enzyme. Reducing of the feedback is often addressed by isolating or using a feedback-resistant variant of the enzyme. Instead, we suggest reducing the level of the molecule causing the feedback, either through diversion of formation of the feedback metabolite, or reducing its level by metabolism (degradation or conversion to a non-feedback active molecule) of the feedback molecule.

One example in the formation of aromatic amino acids. Tyrosine and phenylalanine are synthesized by a final enzyme TyrB, which is inhibited by 3-methyl-2-oxobutanoate. The effects of altering the level of 3-methyl-oxobutanoate would be easiest to see in mutants with ilvE and aspC mutations, the other transaminases that can make the PHE and TYR. If valine is degraded in the cell, the compound 3-methyl-2-oxobutanoate is formed. We can further consume the 3-methyl-2-oxobutanoate by activating it to a CoA-derivative using 3-methyl-2-oxobutanoate dehydrogenase [E.C. 1.2.7.7], this would deplete the 3-methyl-2oxobutanoate level and reduce inhibition of the pathway to the aromatic amino acids PHE and TYR, thereby increasing the level of these desired amino acids.

Another enzyme that could be used to reduce the level of 3-methyl-2-oxobutanoate is Kegg Reaction R01210, 2-oxoisovalerate dehydrogenase, which catalyzes the following:

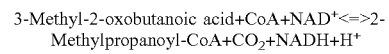

3-Methyl-2-oxobutanoic acid+CoA+NAD$^+$<=>2-Methylpropanoyl-CoA+CO$_2$+NADH+H$^+$ Overexpression of either gene to make these enzymes should deplete the feedback from the 3-methyl-2-oxobutanoate on the transaminase and thus increase formation of PHE or TYR, as compared to when these enzymes are not expressed in excess.

Each of the following references are incorporated herein in their entireties for all purposes:
US20040152159 by Causey.
Alper H., Miyaoku K., Stephanopoulos G., (2005) Construction of lycopene overproducing *E. coli* strains by combining systematic and combinatorial gene knockout targets. Nat. Biotechnol. 23, 612-616.
Blombach B. et al., (2007) l-Valine Production with Pyruvate Dehydrogenase Complex-Deficient *Corynebacterium glutamicum*, Appl. Environ. Microbiol. 73(7): 2079-2084.

Borisov V B, Gennis R B, Hemp J, Verkhovsky M I (2011) The cytochrome bd respiratory oxygen reductases. *Biochim Biophys Acta* 1807: 1398-1413.

Cunningham F. X. Jr., et al., (1994) Molecular structure and enzymatic function of lycopene cyclase from the cyanobacterium *Synechococcus* sp strain PCC7942. Plant Cell 6:1107-1121.

Farmer W. R., Liao J. C., (2000) Improving lycopene production in *Escherichia coli* by engineering metabolic control. Nat. Biotechnol. 18, 533-537.

Hassan B H, Cronan J E (2011) Protein-protein interactions in assembly of lipoic acid on the 2-oxoacid dehydrogenases of aerobic metabolism. J. of Biol. Chem. 286: 8263-8276

Hermes F A, Cronan J E (2009) Scavenging of cytosolic octanoic acid by mutant LplA lipoate ligases allows growth of *Escherichia coli* strains lacking the LipB octanoyltransferase of lipoic acid synthesis. *Journal of bacteriology* 191: 6796-6803

Iram S H, Cronan J E (2006) The beta-oxidation systems of *Escherichia coli* and *Salmonella enterica* are not functionally equivalent. *Journal of bacteriology* 188: 599-608.

Kameda K, Imai Y (1985) Isolation and characterization of the multiple charge isoforms of acyl-CoA synthetase from *Escherichia coli*. *Biochim Biophys Acta* 832: 343-350.

Londer Y Y (2011) Expression of recombinant cytochromes c in *E. coli*. *Methods Mol Biol* 705: 123-150.

Lu P., (2007) Absolute protein expression profiling estimates the relative contributions of transcriptional and translational regulation. Nature Biotechnol. 25: 117-124

Morris T. W., (1995) Lipoic acid metabolism in *Escherichia coli*: the lplA and lipB genes define redundant pathways for ligation of lipoyl groups to apoprotein. *Journal of bacteriology* 177: 1-10.

Perham R N (1991) Domains, motifs, and linkers in 2-oxo acid dehydrogenase multienzyme complexes: a paradigm in the design of a multifunctional protein. Biochem. 30:8501-8512.

Peters-Wendisch P., (2012) Biotin protein ligase from *Corynebacterium glutamicum*: role for growth and L:-lysine production, Appl, Microbiol, Biotechnol. 93(6): 2493-502.

Reed K. E., Cronan J. E., Jr. (1993) Lipoic acid metabolism in *Escherichia coli*: sequencing and functional characterization of the lipA and lipB genes. J. Bacteriol. 175:1325-1336.

Schellhorn H. E., Hassan H. M. (1988) Isolation and characterization of respiratory-deficient mutants of *Escherichia coli* K-12. J. Bacteriol. 170: 78-83.

Spencer J B, Stolowich N J, Roessner C A, Scott A I (1993) The *Escherichia coli* cysG gene encodes the multifunctional protein, siroheme synthase. FEBS Lett. 335: 57-60.

Stolz M, et al., (2007) Reduced folate supply as a key to enhanced L-serine production by *Corynebacterium glutamicum*, Appl. Environ. Microbiol. 73(3):750-5.

Taboada, H., et al. (2008) Thiamine limitation determines the transition from aerobic to fermentative-like metabolism in *Rhizobium etli* C E3, FEMS Microbiology Letters 279(1): 48-55.

Thony-Meyer L (1997) Biogenesis of respiratory cytochromes in bacteria. Microbiol. Mol. Biol. Rev. 61: 337-376.

Tsai C. H., et al., (2000) Novel recombinant hemoglobin, rHb (beta N108Q), with low oxygen affinity, high cooperativity, and stability against autoxidation. Biochem. 39: 13719-13729.

Vadali R. V., et al. (2005) Enhanced lycopene productivity by manipulation of carbon flow to isopentenyl diphosphate in *Escherichia coli*, Biotechnol. Prog. 21, 1558-1561.

Varnado C. L., et al., (2013) Development of recombinant hemoglobin-based oxygen carriers, Antioxid. Redox Signal 18:2314-2328.

Warren M. J., et al., (1994) Gene dissection demonstrates that the *Escherichia coli* cysG gene encodes a multifunctional protein, Biochem J 302(Pt 3): 837-844.

Warren M. J., et al., (1990) The *Escherichia coli* cysG gene encodes S-adenosylmethionine-dependent uroporphyrinogen III methylase, Biochem J. 265: 725-729.

Yazaki K., et al., (2002) Geranyl diphosphate:4-hydroxybenzoate geranyltransferase from *Lithospermum erythrorhizon*. Cloning and characterization of a key enzyme in shikonin biosynthesis, J. Biol. Chem. 277, 6240-6246.

We claim:

1. A method of increasing the production of a product in a bacteria, said method comprising:
   a) providing a bacteria having a product pathway producing a product, wherein a competitive pathway competes with said product pathway for available carbon, said competitive pathway requiring a cofactor that is not rate limiting;
   b) introducing one or more diverting gene(s) under the control of a promoter into said bacteria to directly or indirectly divert said cofactor or an intermediate in the formation of the cofactor away from said competitive pathway;
   c) allowing expression of said diverting gene(s) and reducing levels of said cofactor, and thus reducing levels of said competitive pathway;
   d) thereby increasing said product pathway and said product;
   wherein said cofactor and said one or more diverting genes and said products are selected from the group consisting of:

| Cofactor: | Diverting gene(s) encoding: | Product: |
| --- | --- | --- |
| ubiquinone | geranylgeranyl diphosphate synthase and phytoene synthase and phytoene desaturase | Fermentative products or lactate or acetate ethanol or formate, or acetate or succinate or 2,3 butane diol |
| ubiquinone | geranyl diphosphate: 4-hydroxybenzoate geranyltransferase | Fermentative products or lactate or acetate ethanol or formate, or acetate or succinate or 2,3 butane diol |
| biotin | Biotin-CoA ligase or biotin CoA synthetase | Glutamate or lysine |
| pantothenate | pantothenate hydrolyase | Valine |
| thiamine | thiamine pyridinylase or aminopyrimidine aminohydrolase | Fermentative products or lactate or ethanol or formate, or acetate or succinate or 2,3 butane diol pr |
| Folate or 4-aminobenzoate | 4-aminobenzoate 1-monooxygenase or aminobenzoate decarboxylase | Serine |
| Heme | Siroheme synthase | Fermentative products or lactate or acetate ethanol or formate or acetate or succinate or 2,3 butane diol |
| 3-Methyl-2-oxobutanoic acid | 2-oxoisovalerate dehydrogenase or 3-methyl-2-oxobutanoate dehydrogenase | PHE or TYR. |

2. The method of claim 1, wherein said promoter is a constitutive promoter.

3. The method of claim 1, wherein said promoter is an inducible promoter.

4. The method of claim 1, wherein said bacteria is *E. coli* or *Corynebacterium glutamicum*.

5. The method of claim 1, wherein said cofactor is ubiquinone and said diverting gene(s) is i) crtE, crtB and crtI or ii) PGT-1.

6. The method of claim 1, wherein said cofactor is heme and said diverting gene(s) encodes siroheme synthase.

7. The method of claim 1, wherein said cofactor is thiamine and said diverting gene(s) encodes thiamine pyridinylase or aminopyrimidine aminohydrolase.

* * * * *